United States Patent [19]

Evers et al.

[11] Patent Number: 4,496,775

[45] Date of Patent: Jan. 29, 1985

[54] 1,2,3,3,5,6-HEXAMETHYL-BICYCLO[2.2.2]-OCT-5-EN-2-OL, PROCESS FOR PRODUCING SAME, INTERMEDIATES USEFUL IN SAID PROCESS AND ORGANOLEPTIC USES OF SAME

[75] Inventors: William J. Evers, Locust; Braja D. Mookherjee, Holmdel; Anton Van Ouwerkerk, Livingston, all of N.J.; Augustinus G. Van Loveren, Rye, N.Y.

[73] Assignee: International Flavors & Fragrances Inc., New York, N.Y.

[21] Appl. No.: 602,581

[22] Filed: Apr. 20, 1984

Related U.S. Application Data

[62] Division of Ser. No. 535,800, Sep. 26, 1983, , which is a division of Ser. No. 371,930, Apr. 26, 1982, Pat. No. 4,434,085.

[51] Int. Cl.³ ............................................. C07C 35/22

[52] U.S. Cl. ................................. 568/820; 252/522 R; 252/526

[58] Field of Search ..................... 568/820; 252/522 R

[56] References Cited

U.S. PATENT DOCUMENTS

| | | | |
|---|---|---|---|
| 3,869,524 | 3/1975 | Light et al. | 252/522 R |
| 3,914,322 | 10/1975 | Chappell et al. | 568/820 |
| 3,914,932 | 10/1975 | Terkaiki et al. | 58/50 |
| 3,929,676 | 12/1975 | Chappell et al. | 252/522 R |
| 3,948,818 | 4/1976 | Tomlyans et al. | 252/526 |
| 3,967,629 | 7/1976 | Chappell et al. | 121/144 |
| 4,434,085 | 2/1984 | Evers et al. | 568/820 |

Primary Examiner—Werren B. Lone
Attorney, Agent, or Firm—Arthur L. Liberman

[57] ABSTRACT

Described is 1,2,3,3,5,6-hexamethyl-bicyclo[2.2.2]oct-5-en-2-ol as a mixture of isomers and in its isomeric forms and the uses thereof in augmenting or enhancing the aroma of perfume compositions, perfumed articles, and colognes.

4 Claims, 27 Drawing Figures

GLC PROFILE FOR EXAMPLE I

IR SPECTRUM FOR PEAK 101 OF FIG.1 FOR EXAMPLE I.

NMR SPECTRUM FOR PEAK 101 OF FIG.1, EXAMPLE I.

GLC PROFILE FOR EXAMPLE II.

MASS SPECTRUM FOR PEAK 501 OF FIG. 5, EXAMPLE II.

NMR SPECTRUM FOR PEAK 501 OF FIG. 5, EXAMPLE II.

IR SPECTRUM FOR PEAK 501 OF FIG. 5 FOR EXAMPLE II.

GLC PROFILE FOR EXAMPLE III.

MASS SPECTRUM FOR PEAK 901 OF FIG.9, EXAMPLE III.

IR SPECTRUM FOR PEAK 901 OF FIG.9 FOR EXAMPLE III.

NMR SPECTRUM FOR PEAK 901 OF FIG.9, EXAMPLE III.

MASS SPECTRUM FOR PEAK 902 OF FIG.9, EXAMPLE III.

IR SPECTRUM FOR PEAK 902 OF FIG.9 FOR EXAMPLE III.

NMR SPECTRUM FOR PEAK 902 OF FIG.9, EXAMPLE III.

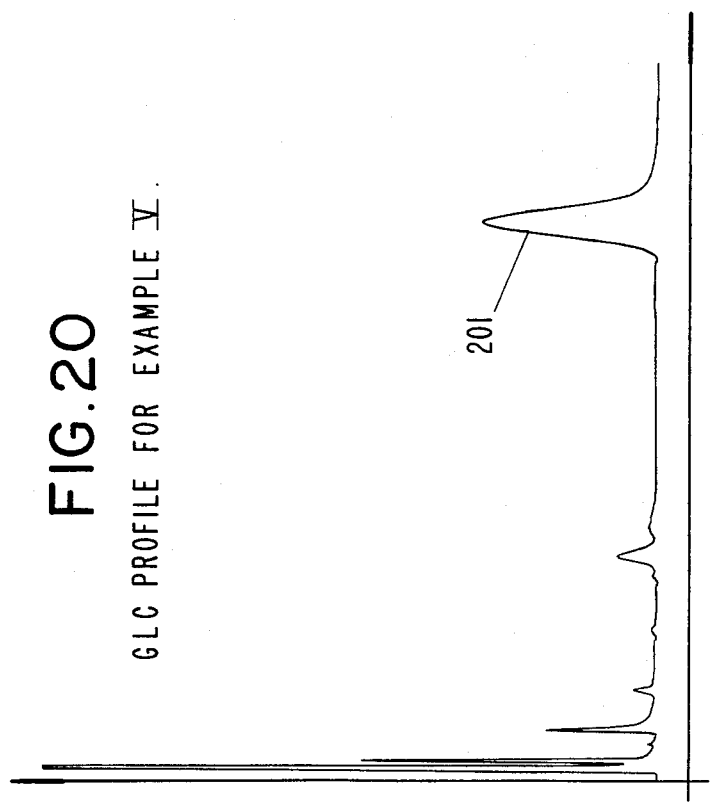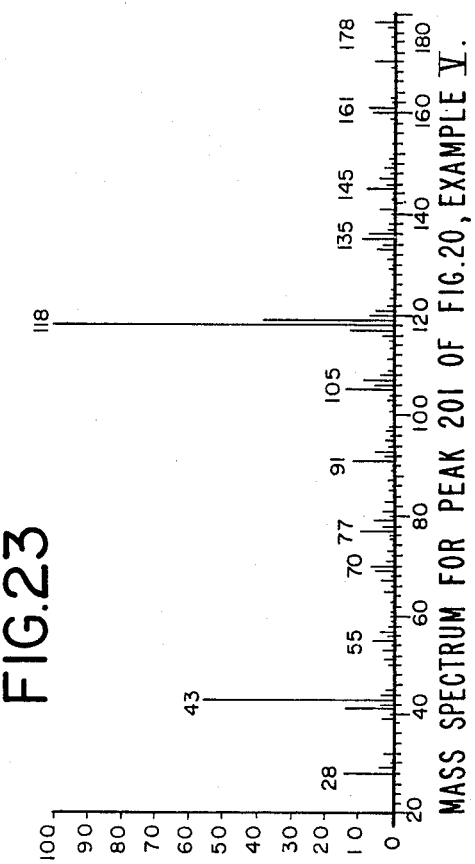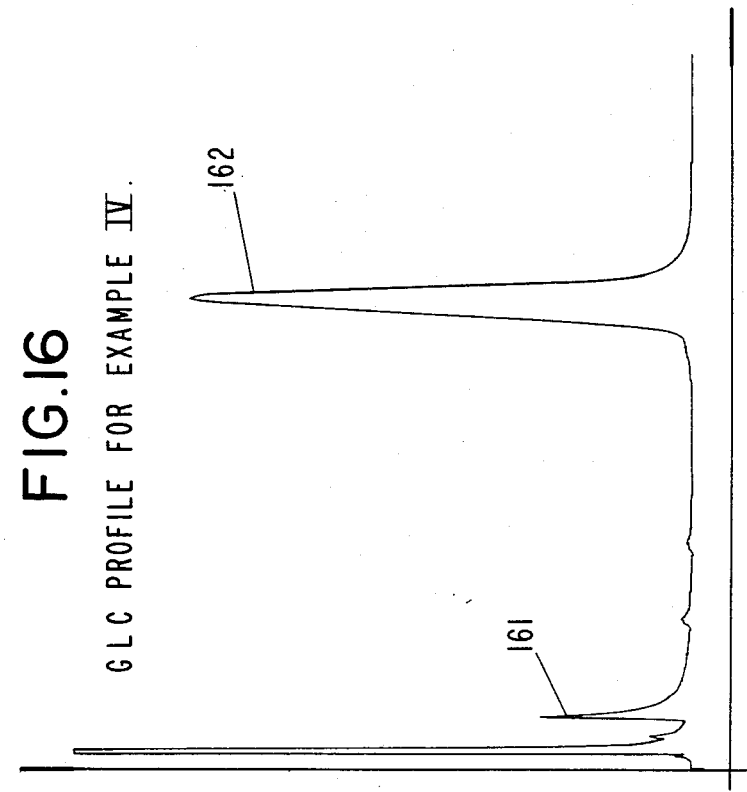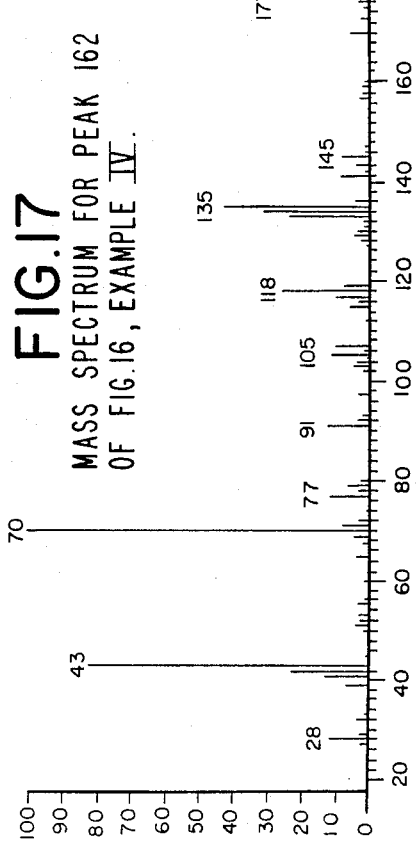

IR SPECTRUM FOR PEAK 162 OF FIG.16 FOR EXAMPLE IV.

IR SPECTRUM FOR PEAK 201 OF FIG. 20 FOR EXAMPLE V.

NMR SPECTRUM FOR PEAK 201 OF FIG. 20, EXAMPLE V.

GLC PROFILE FOR EXAMPLE VI.

GLC PROFILE FOR EXAMPLE XX.

GLC PROFILE FOR EXAMPLE XX (B)

GLC PROFILE FOR EXAMPLE XX (A)

1,2,3,3,5,6-HEXAMETHYL-BICYCLO[2.2.2]-OCT-5-EN-2-OL, PROCESS FOR PRODUCING SAME, INTERMEDIATES USEFUL IN SAID PROCESS AND ORGANOLEPTIC USES OF SAME

This is a divisional of application Ser. No. 535,800, filed Sept. 26, 1983, which in turn, is a divisional of application for U.S. Letters Patent, Ser. No. 371,930 filed on Apr. 26, 1982 now U.S. Pat. No. 4,434,085 issued Feb. 28, 1984.

BACKGROUND OF THE INVENTION

Our invention describes 1,2,3,3,5,6-hexamethyl-bicyclo[2.2.2]oct-5-en-2-ol and isomers thereof defined according to the structures:

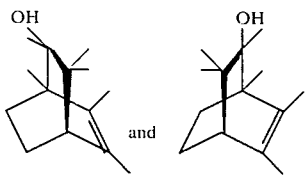

and uses thereof in augmenting or enhancing the aroma of perfume compositions, colognes and perfumed articles.

Bicyclo[2.2.2]octane derivatives are shown to be useful as fragrances in U.S. Pat. Nos. 3,929,676, 3,914,322 and 3,967,629 all of which are incorporated herein by reference. Thus, these patents disclose generically compounds defined according to the structure:

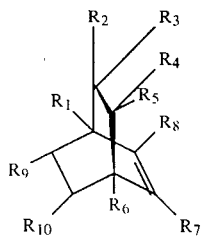

wherein one of $R_2$, $R_3$, $R_4$ and $R_5$ can be hydroxyl and the other of $R_2$, $R_3$, $R_4$ and $R_5$ are methyl or hydrogen and wherein $R_1$, $R_6$, $R_7$, $R_8$, $R_9$ and $R_{10}$ can be methyl or hydrogen. It is indicated also in these patents that these compounds can be useful in augmenting or enhancing perfume compositions and can be used to contribute various woody, camphoraceous, patchouli or floral fragrances. Specifically, these patents disclose perfume uses of the compounds defined according to the structures:

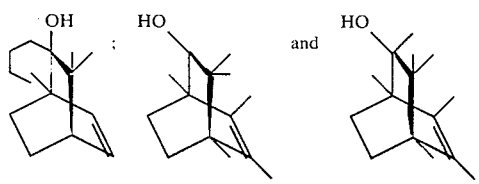

However, the specific compounds of the instant invention defined according to the structures:

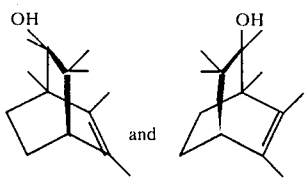

although covered by the generic formula:

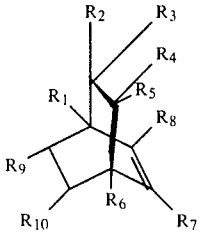

have unexpected, unobvious and advantageous properties insofar as their uses in augmenting or enhancing the aroma of perfumes, perfume compositions and colognes are concerned.

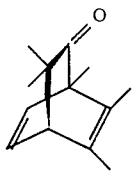

(conditions: SE-30 column programmed from 120° C. to 210° C. at 8° C. per minute).

Figure 2:
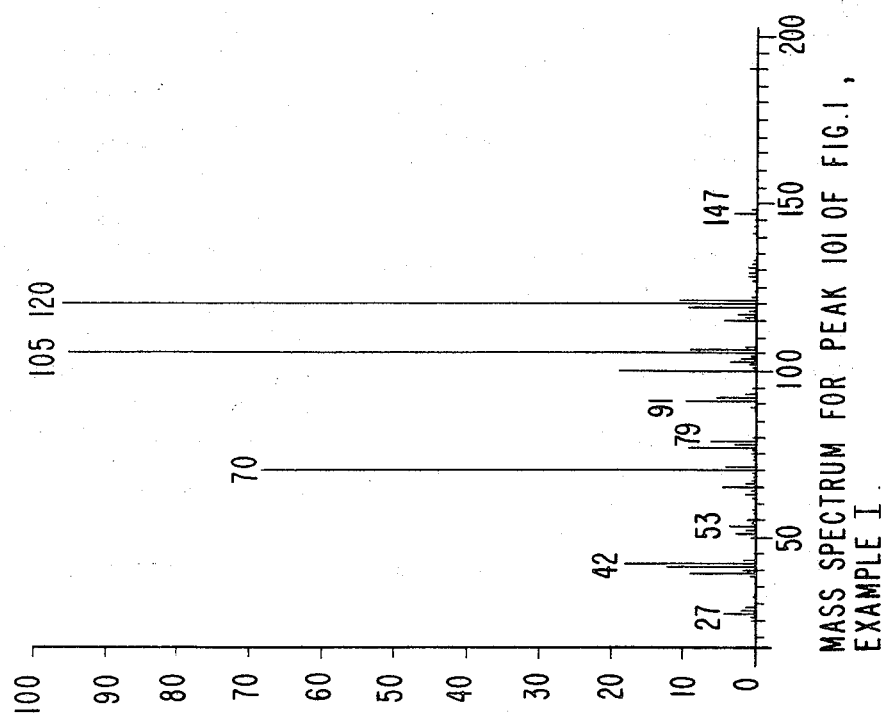
Figure 1:
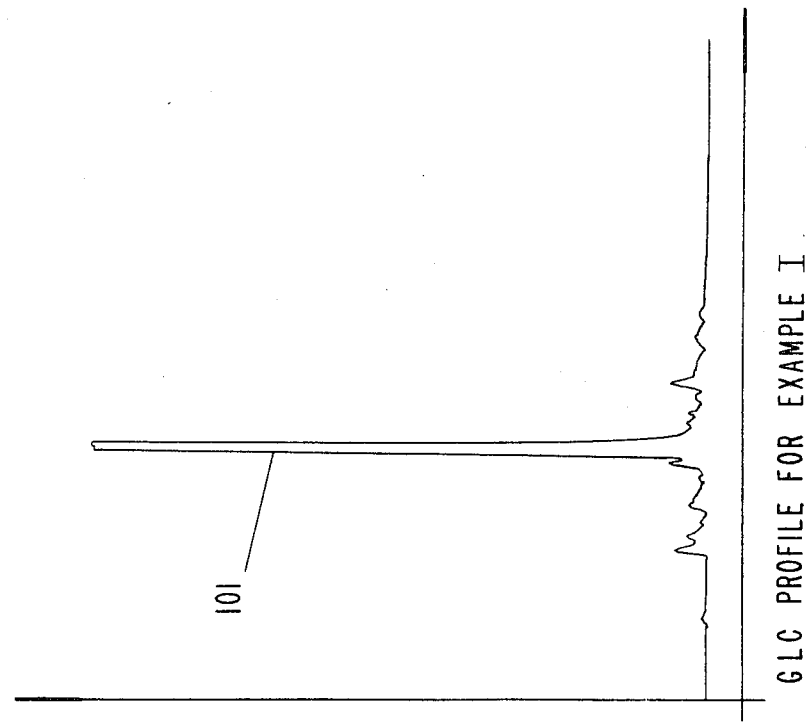
FIG. 1 is the GLC profile for the reaction product of Example I having the structure.

FIG. 2 is the mass spectrum for the peak indicated by reference numeral "101" of FIG. 1 for the compound having structure:

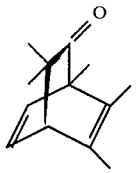

Figure 3:
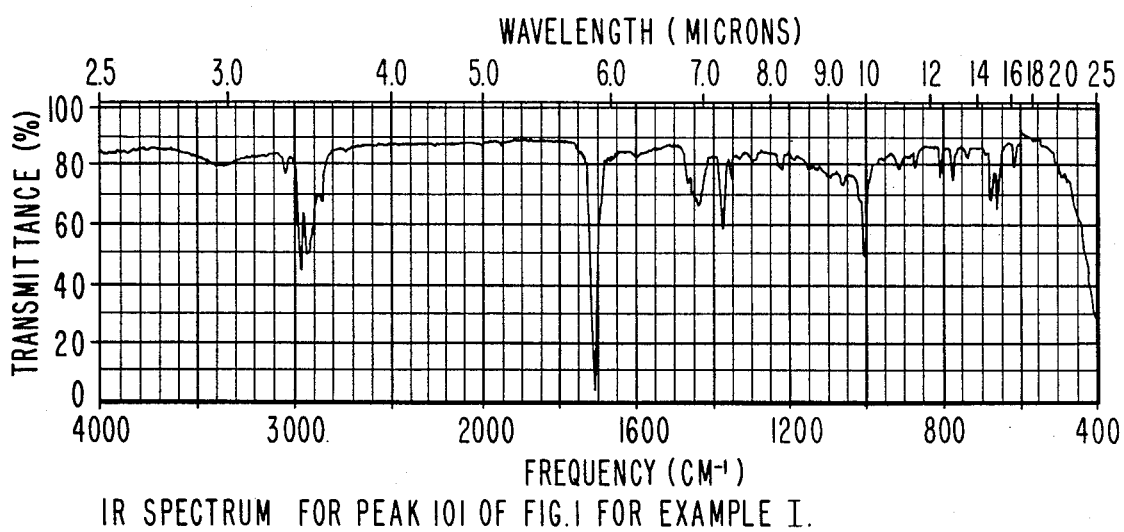

FIG. 3 is the infra-red spectrum for the compound of peak 101 of FIG. 1 having the structure:

Figure 4:
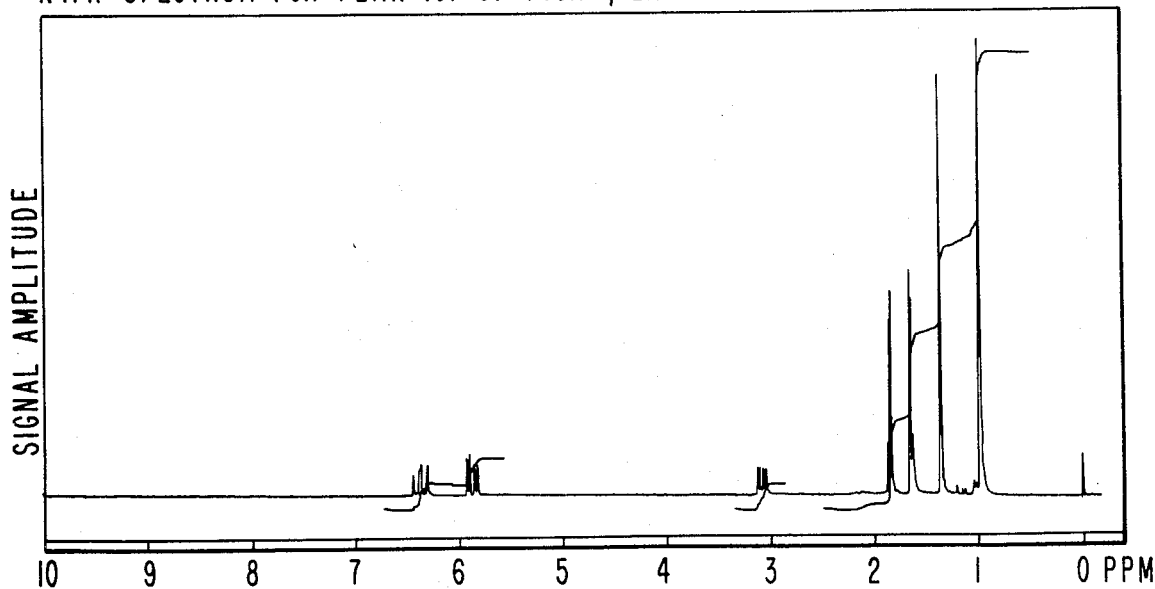

FIG. 4 is the NMR spectrum (Solvent: CFCl$_3$; Field strength 100 MHz) for the peak indicated by reference numeral "101" of FIG. 1 for the compound having the structure:

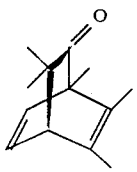

Figure 5:
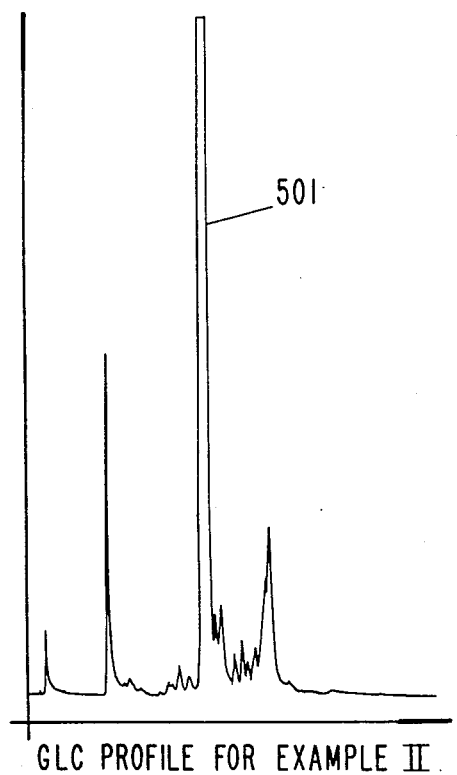

FIG. 5 is the GLC profile for the reaction product of Example II containing the compound defined according to the structure:

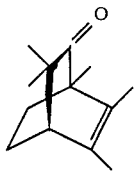

Figure 6:
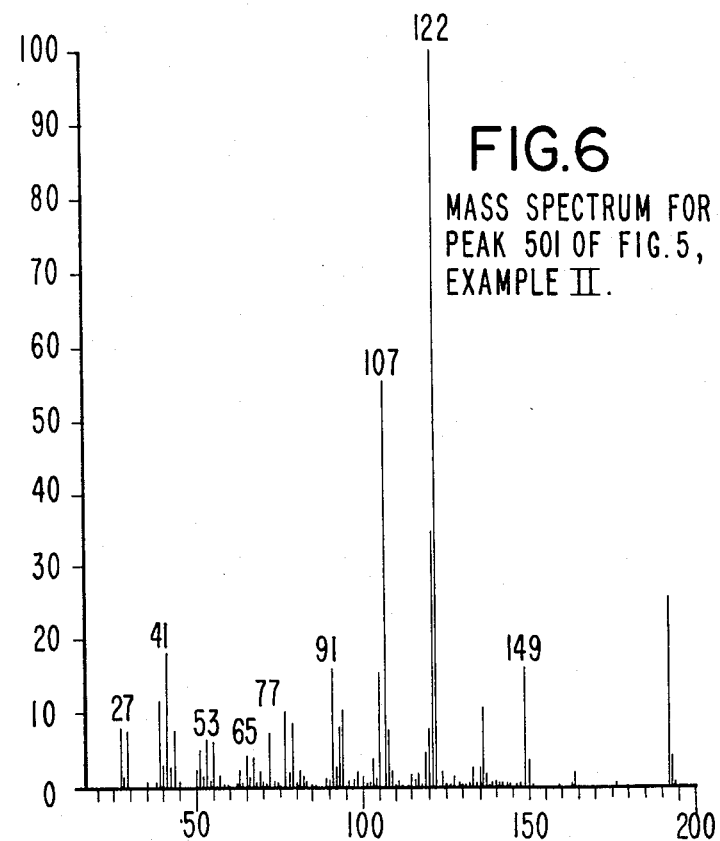

FIG. 6 is the mass spectrum for the compound of peak 501 of FIG. 5 having the structure:

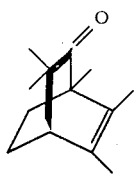

Figure 7:
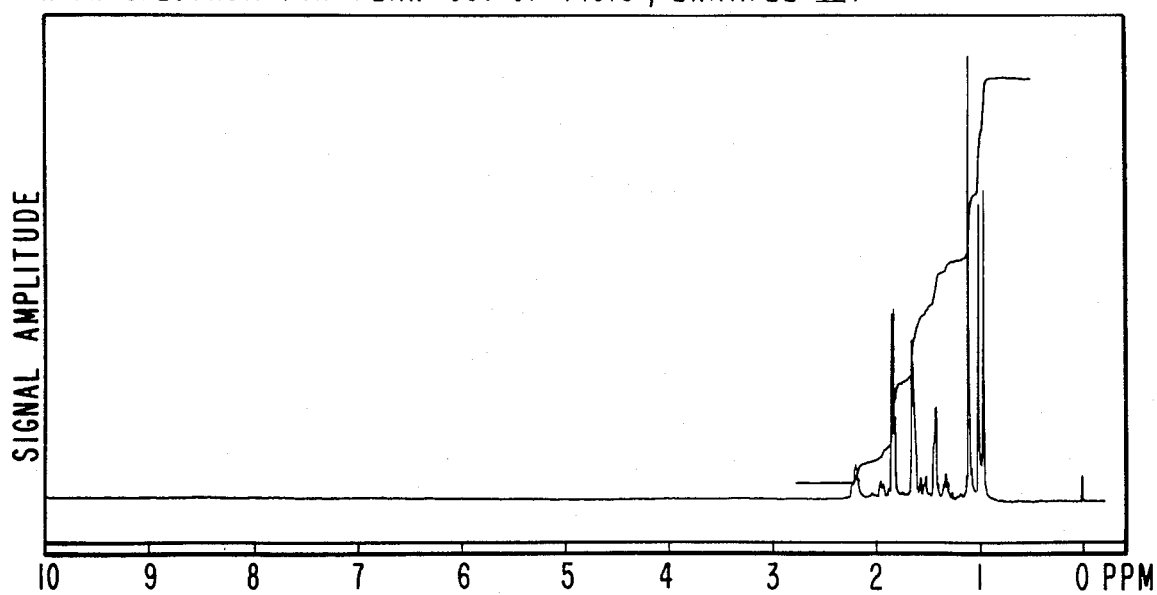

FIG. 7 is the NMR spectrum for the compound of peak 501 of FIG. 5 having the structure:

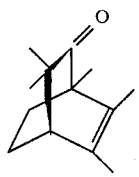

(Solvent: $CFCl_3$; Field strength 100 MHz).

Figure 8:
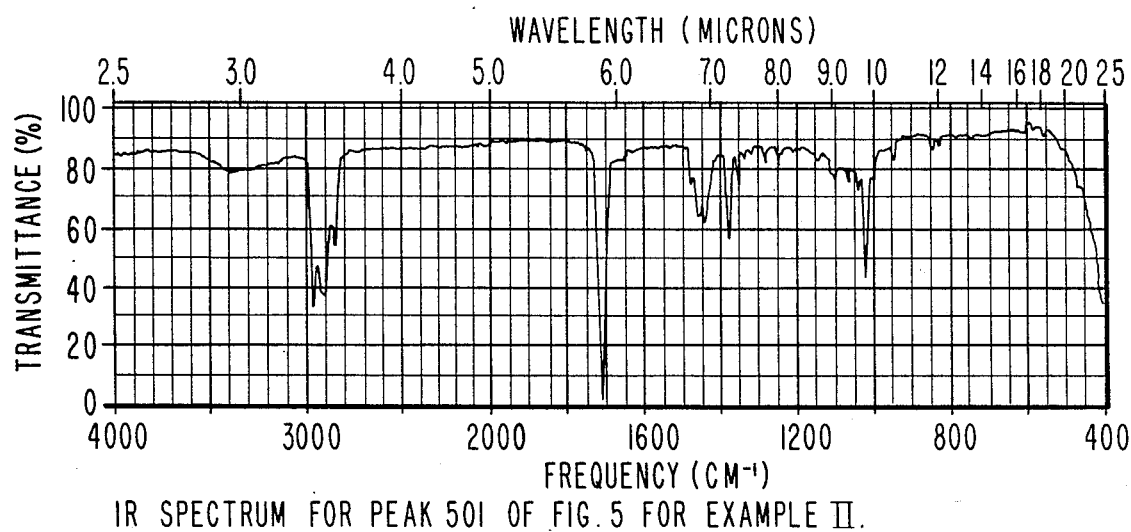

FIG. 8 is the infra-red spectrum for the compound of peak 501 of FIG. 5 having the structure:

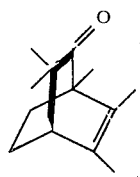

Figure 9:
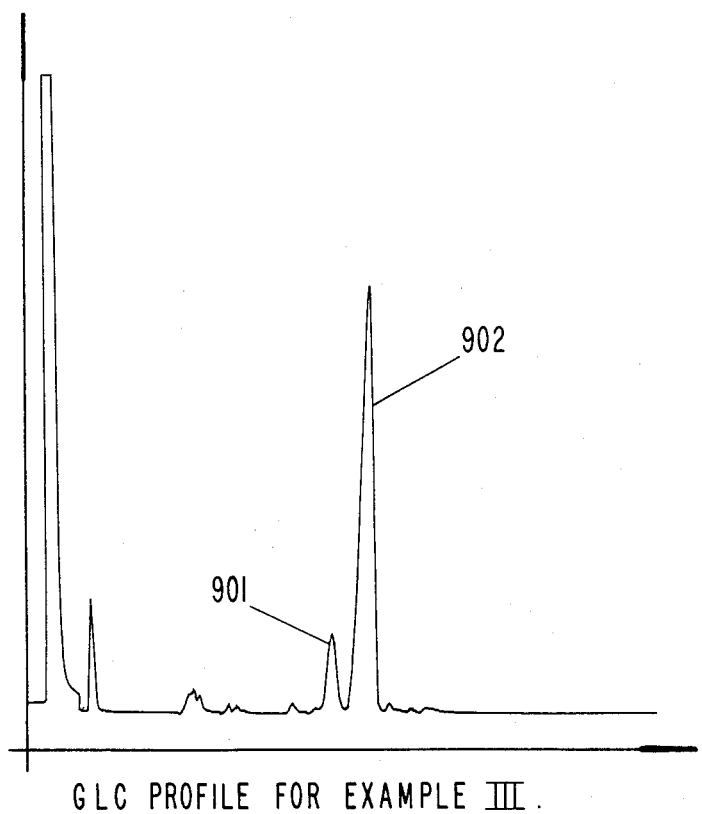

FIG. 9 is the GLC profile for fraction 2 of the distillation product of the reaction product of Example III containing the compounds defined according to the structures:

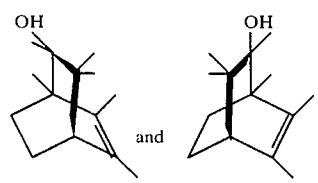

Figure 10:
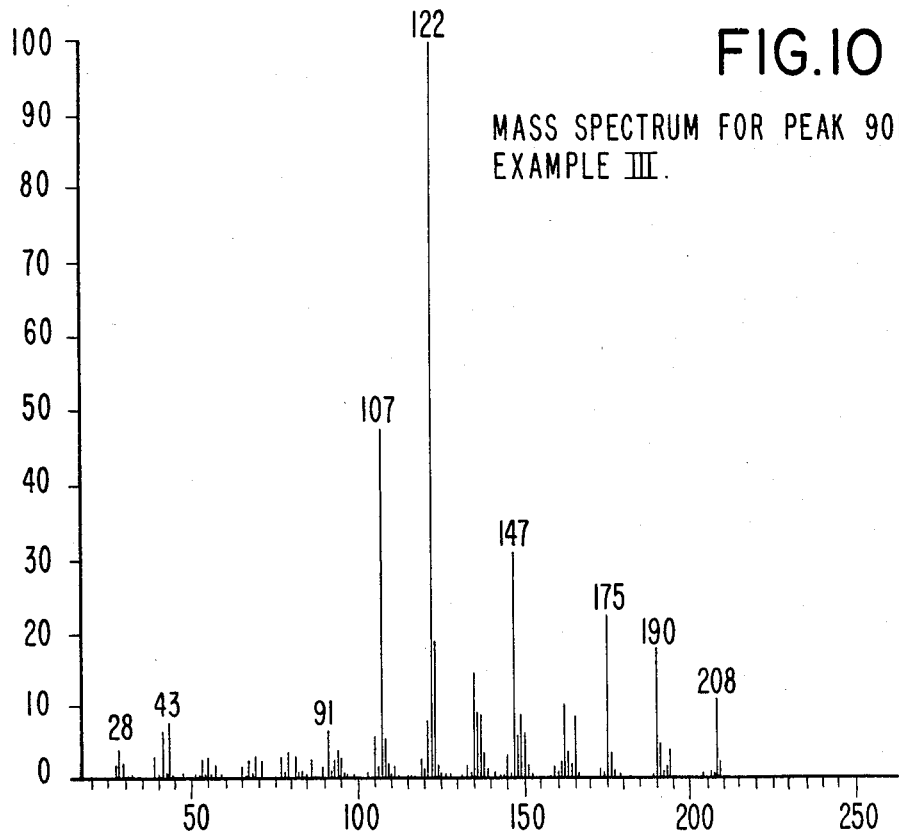

FIG. 10 is the mass spectrum for the peak indicated by reference numeral "901" of FIG. 9 for one of the compounds produced according to Example III having one of the structures:

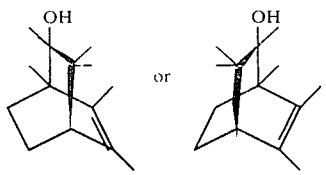

Figure 11:
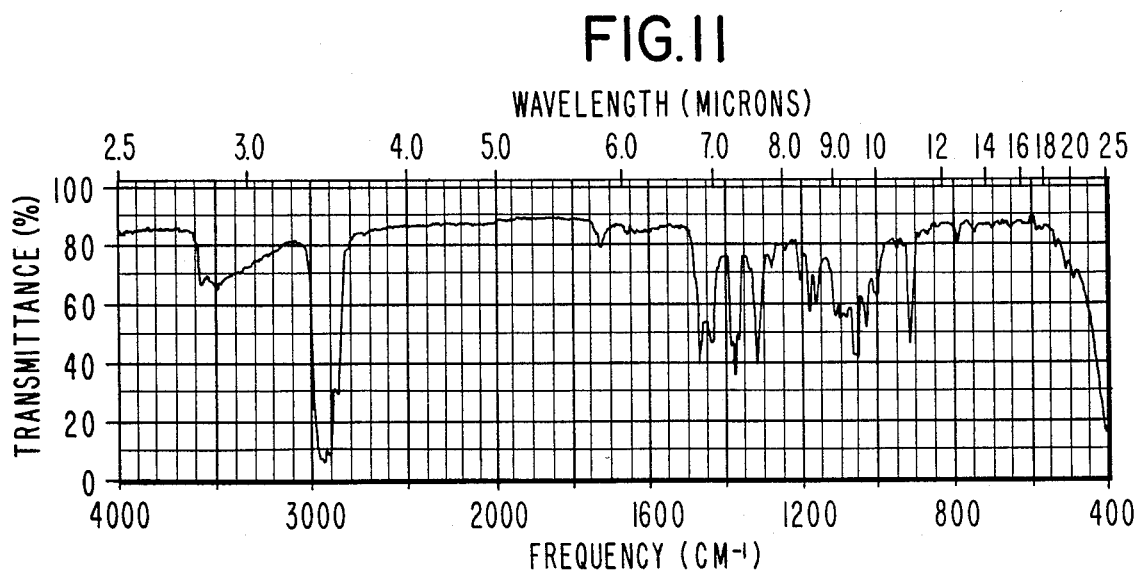

FIG. 11 is the infra-red spectrum for the compound of peak 901 of FIG. 9 having one of the structures:

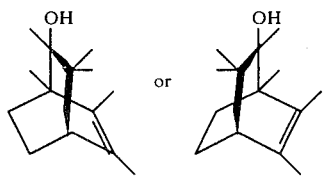

Figure 12:
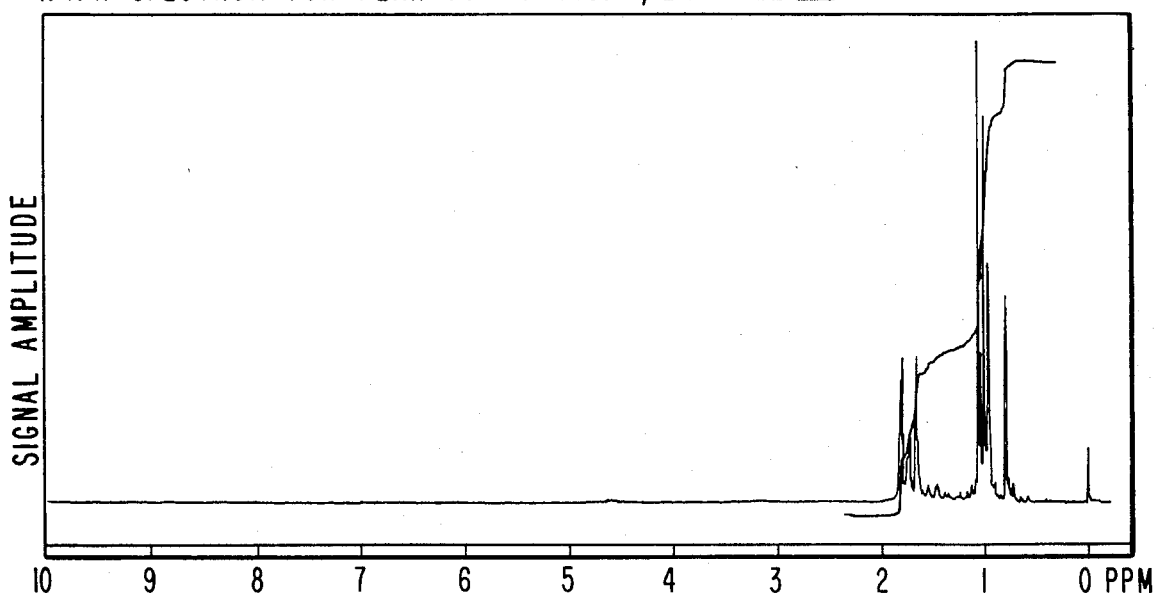

FIG. 12 is the NMR spectrum for the compound of peak 901 of FIG. 9 produced according to Example III containing one of the compounds having the structures:

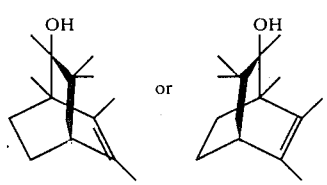

(Solvent: $CFCl_3$; Field strength 100 MHz).

Figure 13:
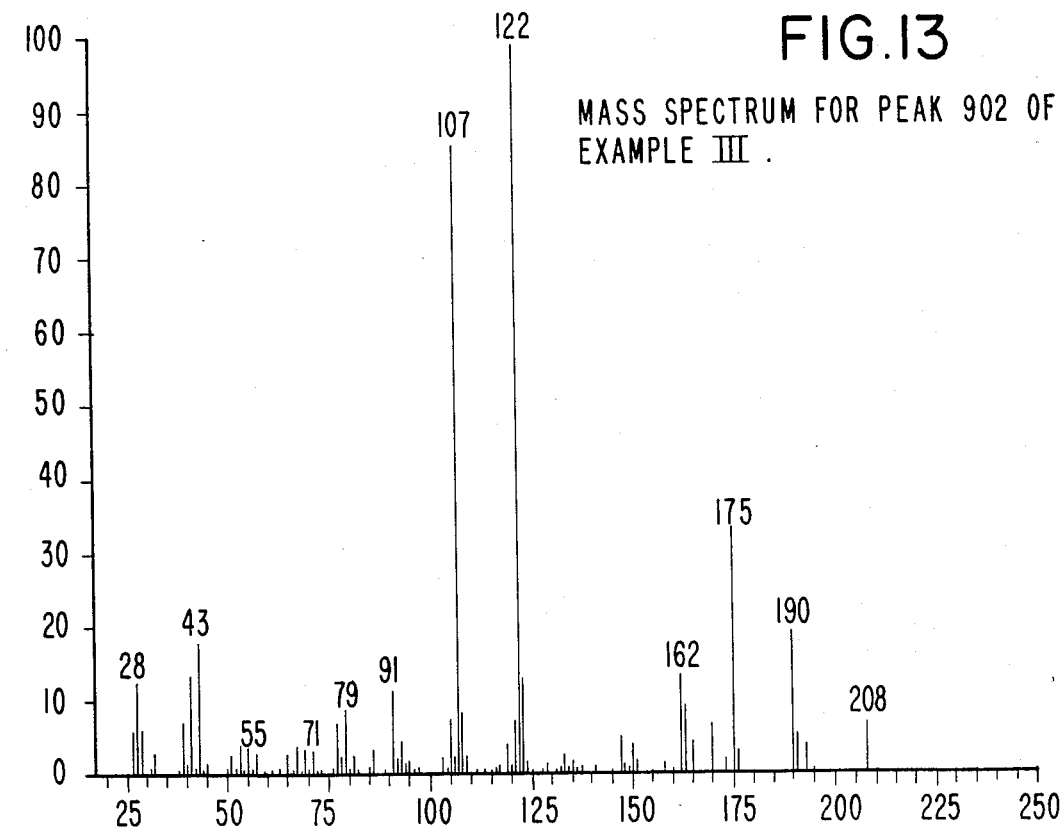

FIG. 13 is the mass spectrum for the peak indicated by reference numeral "902" of FIG. 9 for one of the compounds having the structures:

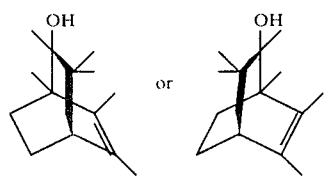

produced according to Example III.

Figure 14:
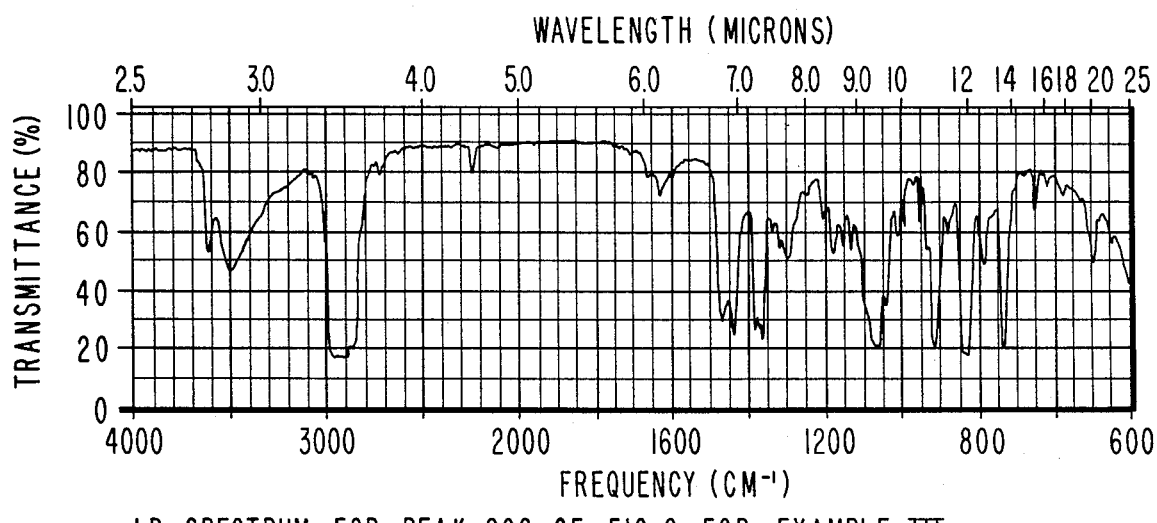

FIG. 14 is the infra-red spectrum for the peak indicated by reference numeral "902" of FIG. 9 for one of the compounds produced according to Example III having one of the structures:

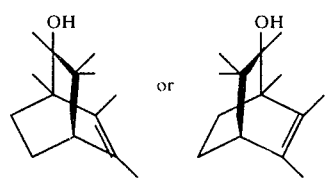

Figure 15:
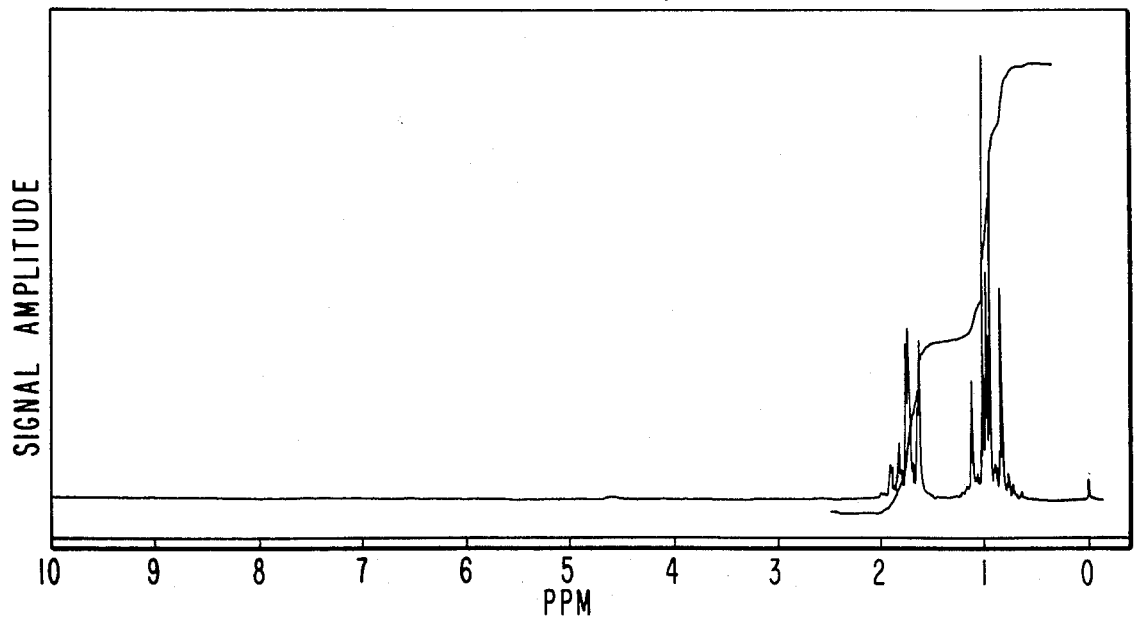

FIG. 15 is the NMR spectrum for the peak indicated by reference numeral "902" of FIG. 9 for one of the compounds produced according to Example III having one of the structures:

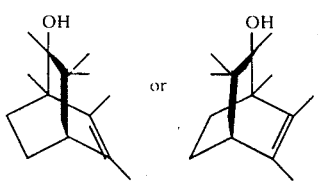

or

FIG. 16 is the GLC profile for the reaction product of Example IV containing the compound having the structure:

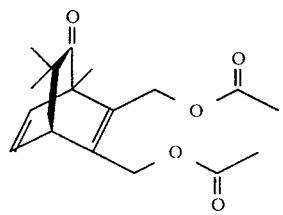

FIG. 17 is the mass spectrum for the peak indicated by reference numeral "162" of FIG. 16 for the compound produced according to Example IV having the structure:

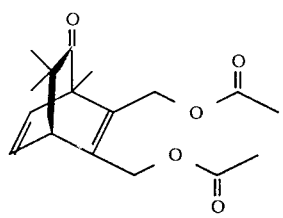

Figure 18:
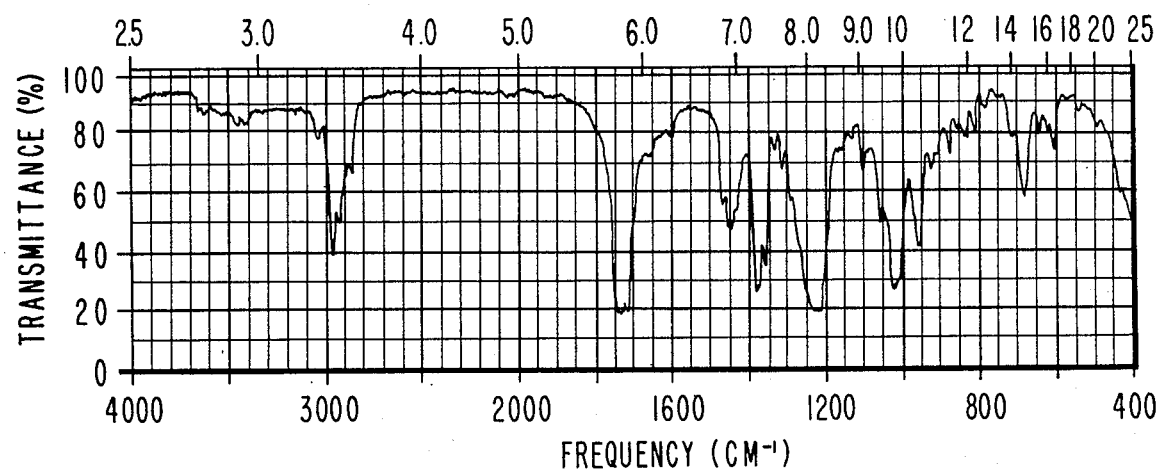

FIG. 18 is the infra-red spectrum for the peak indicated by reference numeral "162" of FIG. 16 for the compound produced according to Example IV having the structure:

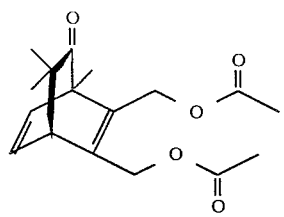

Figure 19:
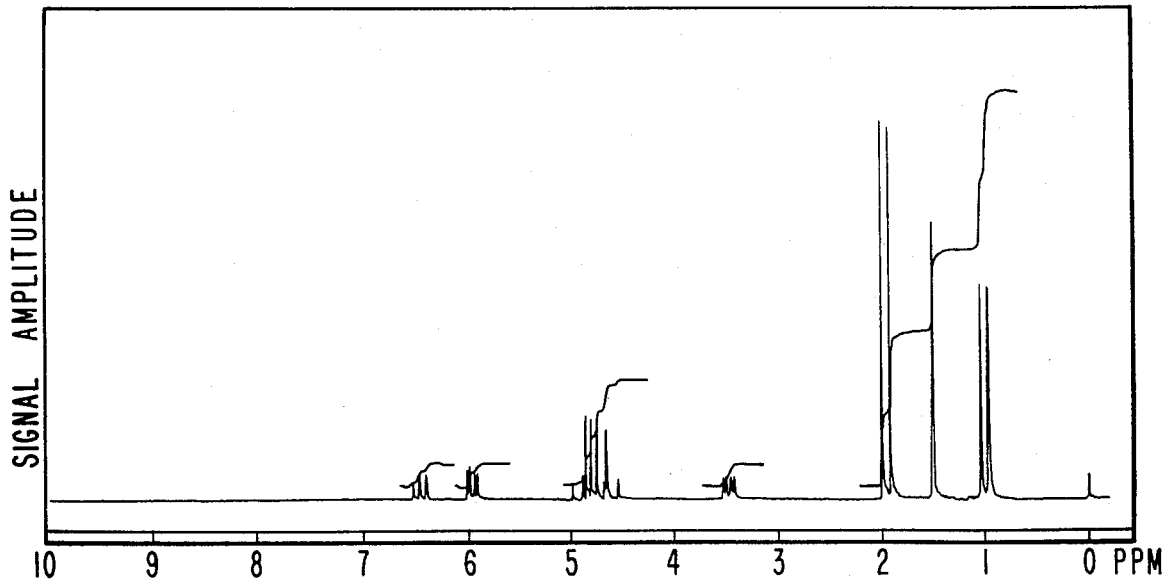

FIG. 19 is the NMR spectrum for the compound of the peak indicated by reference numeral "162" of FIG. 16 for the compound produced according to Example IV having the structure:

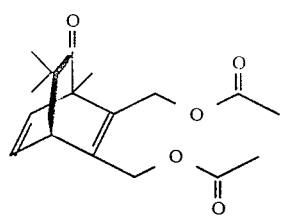

FIG. 20 is the GLC profile for the reaction product of Example V containing the compound defined according to the structure:

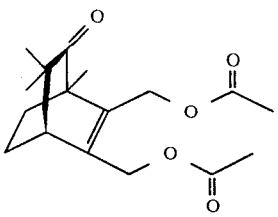

Figure 21:
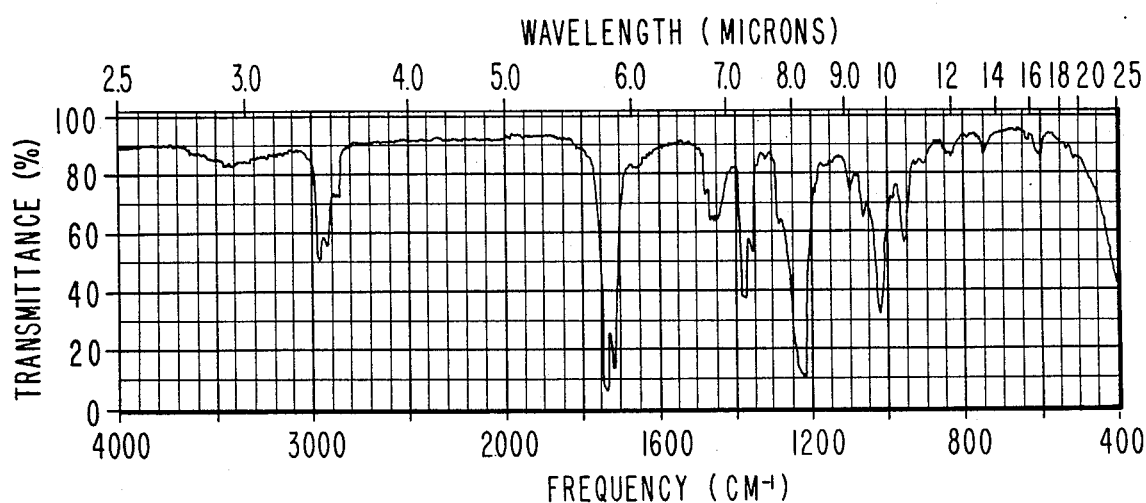

FIG. 21 is the infra-red spectrum for the compound of peak 201 of FIG. 20 which is for the compound produced according to Example V having the structure:

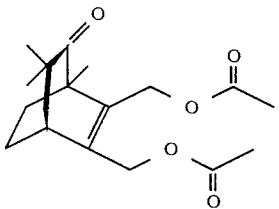

Figure 22:
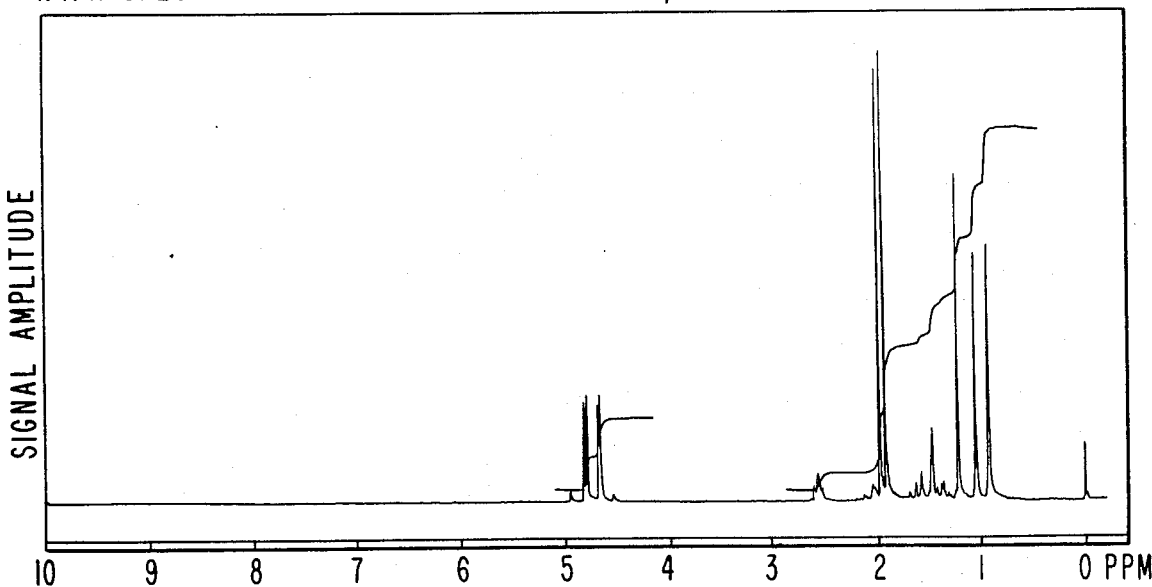

FIG. 22 is the NMR spectrum for the compound of the peak indicated by reference numeral "201" of FIG. 20, the compound produced according to Example V having the structure:

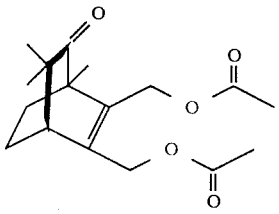

(Solvent: CFCl$_3$; Field strength 100 MHz).

FIG. 23 is the mass spectrum for the compound of the peak indicated by reference numeral "201" of FIG. 20, the compound produced according to Example V having the structure:

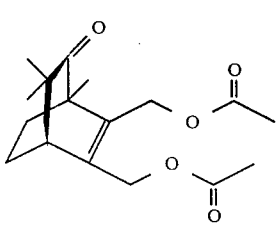

Figure 24:
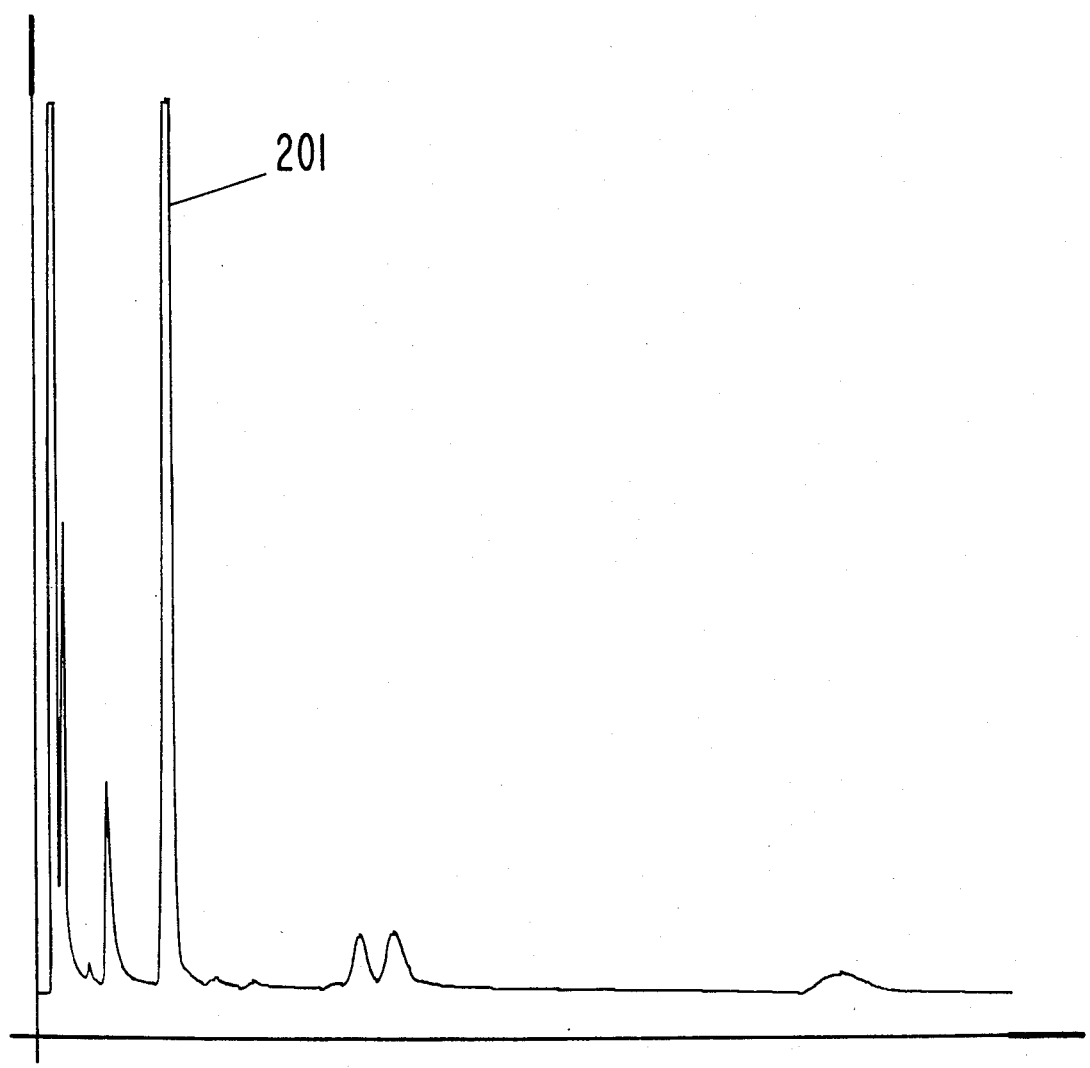

FIG. 24 is the GLC profile for the reaction product of Example VI containing the compound defined according to the structure:

Figure 25:
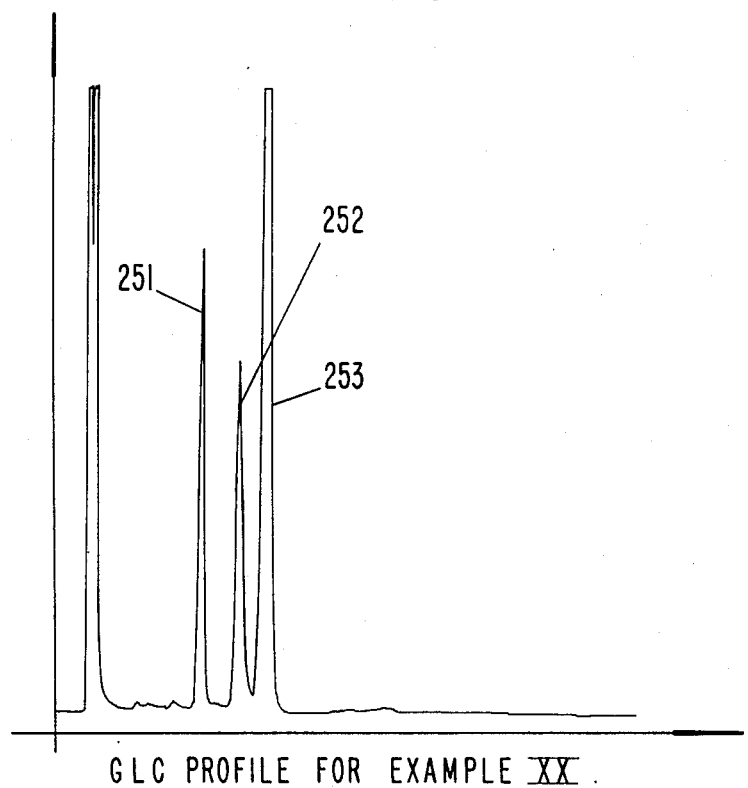

FIG. 25 is the GLC profile for the reaction product of Example XX containing the isomers defined according to the structures:

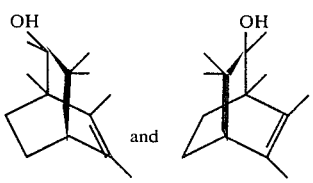

wherein the ratio of isomers is 1:3.

Figure 26:
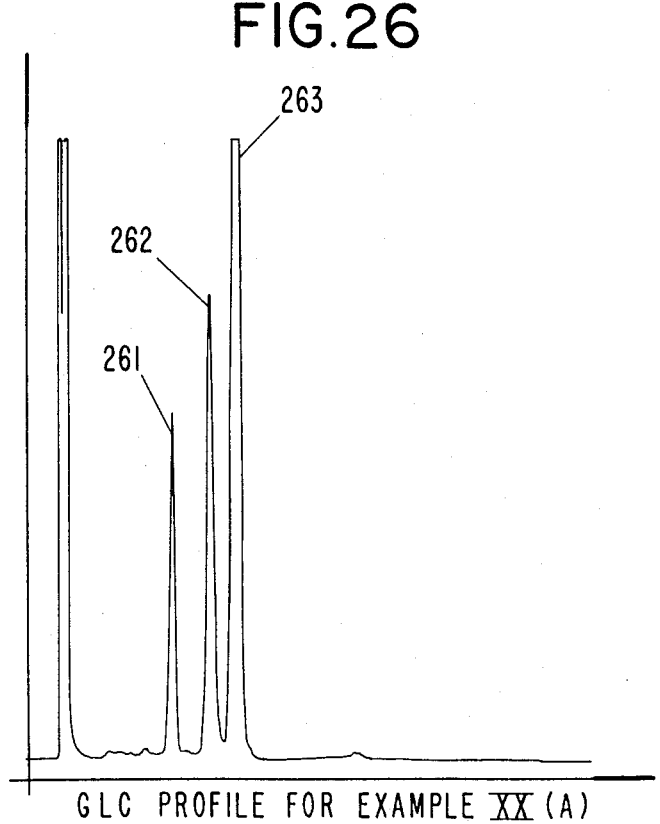

FIG. 26 is the GLC profile of the reaction product of Example XX(A) containing the isomers having the structures:

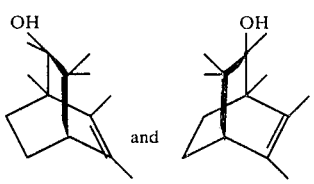

wherein the ratio of isomers is 1:2.2.

Figure 27:
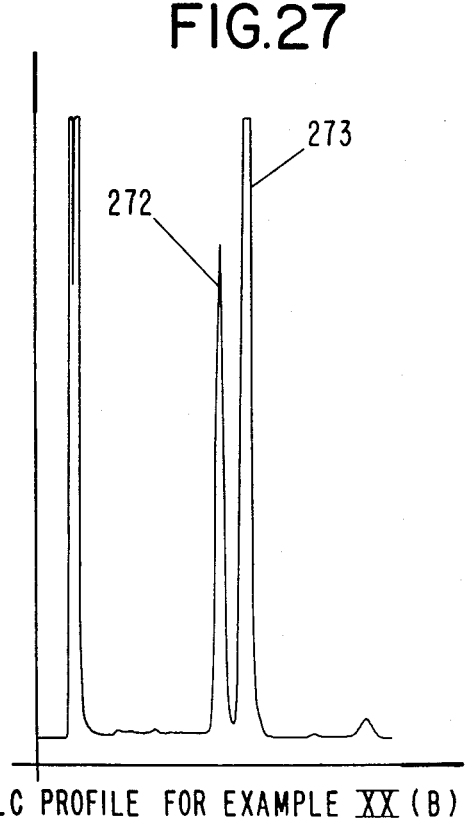

FIG. 27 is the GLC profile for the reaction product of Example XX(B) containing the compounds having the structures:

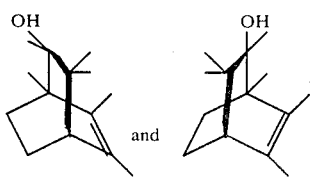

wherein the ratio of the isomers is 1:2.1.

DETAILED DESCRIPTION OF THE DRAWINGS

FIG. 1 is the GLC profile for the reaction product of Example I containing the compound having the structure:

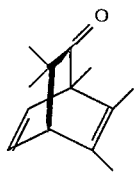

The peak indicated by the reference numeral "101" is for the compound having the structure:

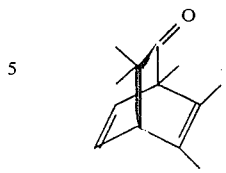

FIG. 5 is the GLC profile for the reaction product of Example II. The peak indicated on FIG. 5 by reference numeral "501" is the peak for the compound having the structure:

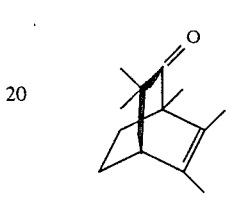

FIG. 9 is the GLC profile for fraction 2 of the distillation product of the reaction product of Example III containing the compounds defined according to the structures:

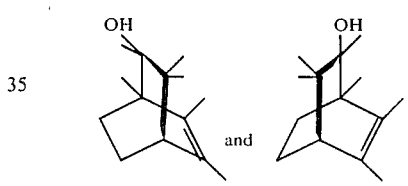

The peaks indicated by reference numerals "901" and "902" are the peaks for the isomers defined according to the structures:

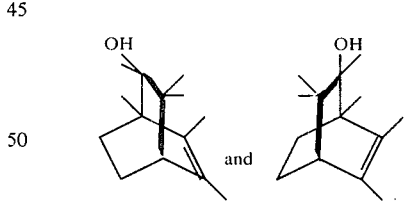

It is uncertain whether peak 901 or 902 is for the isomer having the structure:

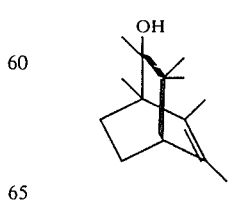

and it is uncertain whether the peak 901 or 902 is for the isomer having the structure:

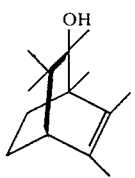

FIG. 16 is the GLC profile for the reaction product of Example IV containing the compound having the structure:

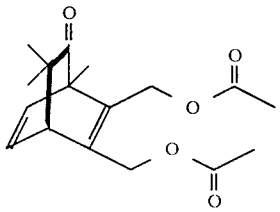

The peak indicated by reference numeral "162" on FIG. 16 is the peak for the reaction product having the structure:

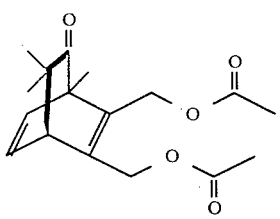

The peak indicated by reference numeral "161" on FIG. 16 is the peak for the starting material for the reaction, having the structure:

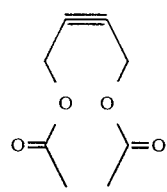

FIG. 20 is the GLC profile for the reaction product of Example V containing the compound having the structure:

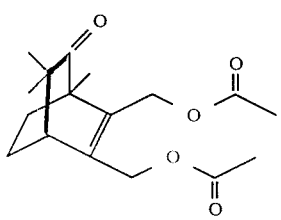

The peak indicated by reference numeral "201" on FIG. 20 is the peak for the compound defined according to the structure:

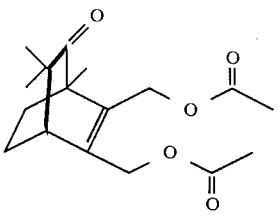

FIG. 24 is the GLC profile for the reaction product of Example VI containing the compound defined according to the structure:

The peak indicated by reference numeral "241" on FIG. 24 is for the compound defined according to the structure:

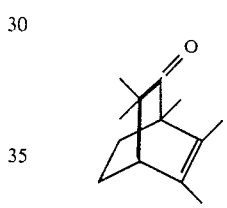

FIG. 25 is the GLC profile for the reaction product of Example XX containing the isomers having the structures:

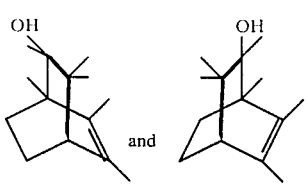

(conditions: SE-30 column operated isothermally at 210° C.). The ratio of isomers is 1:3. The peak indicated by reference numeral "251" is the peak for the starting material having the structure:

The peak indicated by reference numeral "252" is for one of the isomers having the structures:

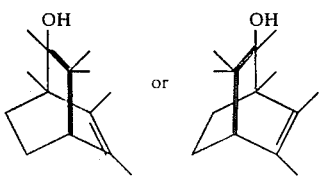

The peak indicated by reference numeral "253" is for one of the isomers:

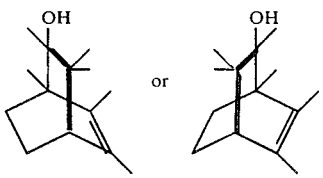

FIG. 26 is the GLC profile for the reaction product of Example XX(A) (reaction operated at 30° C.). Conditions: SE-30 column operated isothermally at 210° C. The ratio of product isomers having the structures:

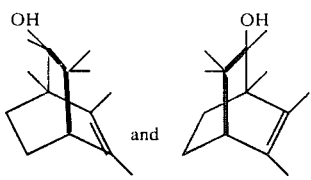

is 1:2.2. The peak indicated by reference numeral "261" is the peak for the starting material having the sturcture:

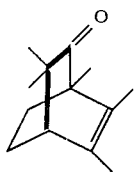

The peak indicated by reference numeral "262" is for one of the isomers having the structures:

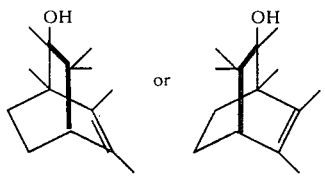

The peak indicated by reference numeral "263" is for one of the isomers having the structure:

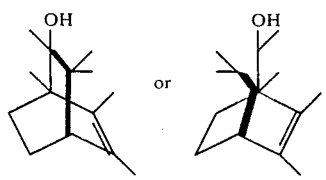

FIG. 27 is the GLC profile for the reaction product of Example XX(B) (reaction operated at 55° C.). Conditions: SE-30 column operated isothermally at 210° C. The ratio of isomers having the structures:

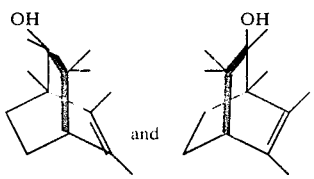

is 1:2.1. The peak indicated by reference numeral "272" is for one of the isomers having the structure:

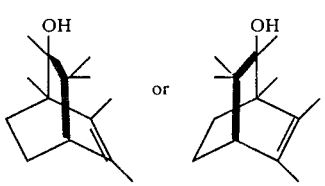

The peak indicated by reference numeral "273" is for one of the isomers having the structure:

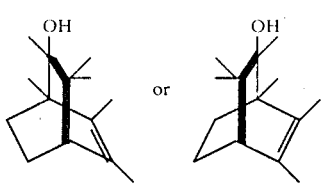

THE INVENTION

The present invention involves the use of 1,2,3,3,5,6-hexamethyl-bicyclo[2.2.2]oct-5-en-2-ol in the form of an isomeric mixture or as individual isomers defined according to the structures:

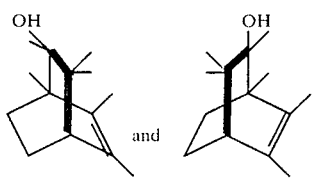

as well as a process for preparing these isomers; and in addition, the perfume uses of these isomers and intermediates useful in carrying out the process for preparing these isomers.

The 1,2,3,3,5,6-hexamethyl-bicyclo[2.2.2]oct-5-en-2-ol produced according to the processes of our invention has fresh, strong, patchouli, ginger and camphoraceous aromas which are very long-lasting and extremely powerful. Even on dry-out the 1,2,3,3,5,6-hexamethyl-bicyclo[2.2.2]oct-5-en-2-ol has excellent, aesthetically pleasing, strong, camphoraceous, patchouli notes. In comparison to the products disclosed in U.S. Pat. Nos. 3,967,629, 3,914,932 and 3,929,676, the 1,2,3,3,5,6-hexamethyl-bicyclo[2.2.2]oct-5-en-2-ol of our invention has a much more intense (3X) longer lasting (4X) than the nearest specifically stated compound or isomer of the aforementioned patents. In any event, the disclosures of the aforementioned patents, U.S. Pat. Nos. 3,929,676, 3,914,932 and 3,967,629 are incorporated herein by reference.

The 1,2,3,3,5,6-hexamethyl-bicyclo[2.2.2]oct-5-en-2-ol of our invention can be prepared in two ways. The first manner of preparing the 1,2,3,3,5,6-hexamethyl-bicyclo[2.2.2]-oct-5-en-2-ol of our invention is disclosed in the aforementioned patents incorporated by reference herein and involves the reaction of dimethyl acetylene having the structure:

with the compound having the structure:

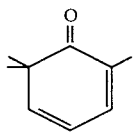

according to the reaction:

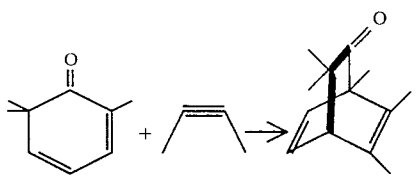

The resulting compound having the structure:

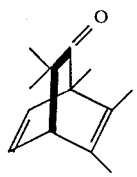

is then hydrogenated according to the reaction:

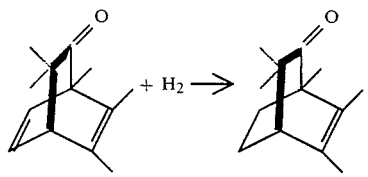

to form the compound having the structure:

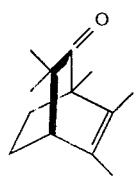

This compound is then reacted with an organometallic compound having the structure:

CH₃M in order to form a mixture of isomers defined according to the structures:

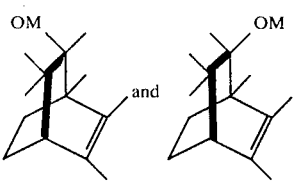

wherein M represents MgX or Li and X represents chloro, bromo or iodo. This reaction is schematically illustrated as follows:

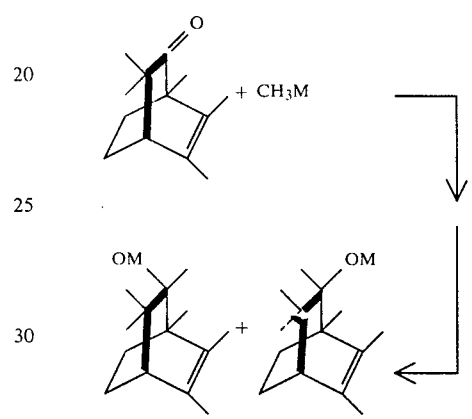

The resulting organometallic compounds defined according to the structures:

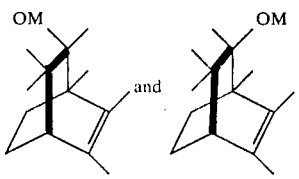

are then treated with weak acid in order to form the mixture of isomers of our invention having the structures:

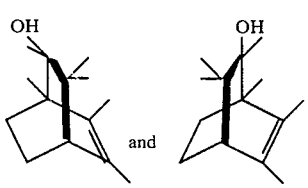

The 1,2,3,3,5,6-hexamethyl-bicyclo[2.2.2]oct-5-en-2-ol of our invention can be prepared according to the novel process of our invention which gives rise to higher conversions and higher yields and is, in general, a more efficient process than the above-mentioned process of the prior art. The novel process of our invention involves firstly, the reaction of the compound having the structure:

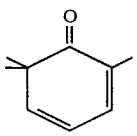

with the compound having the structure:

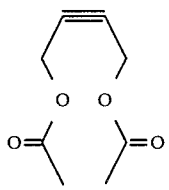

in accordance with the reaction:

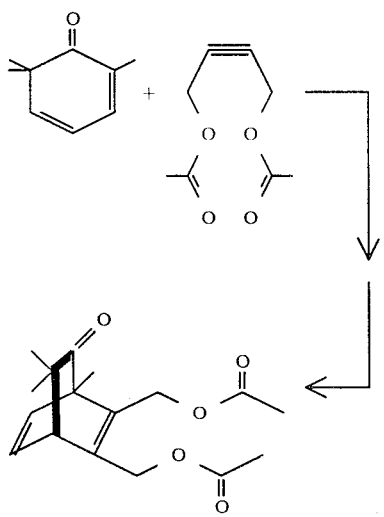

The resulting compound defined according to the structure:

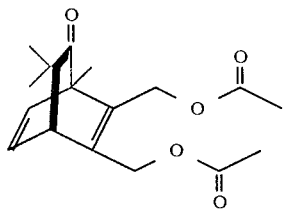

is a novel compound. This compound may be hydrogenated stepwise to first form the compound having the structure:

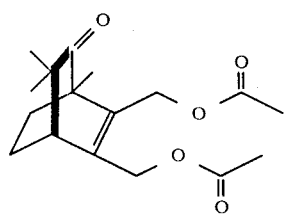

which is then further hydrogenated catalytically to form the ketone defined according to the structure:

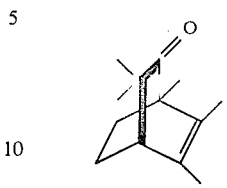

In the alternative, the compound having the structure:

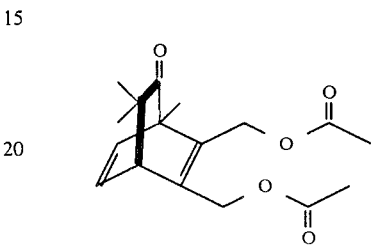

may be hydrogenated with three moles of hydrogen in one step going through the intermediate:

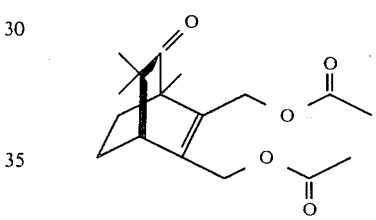

which is not isolated to yield the compound having the structure:

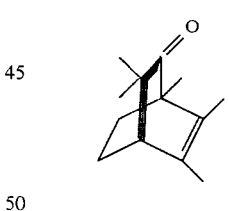

Thereafter, the compound having the structure:

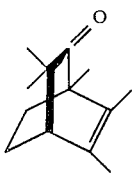

is treated with the compound:

CH₃M is the same manner as set forth supra to ultimately yield the isomers of our invention having the structures:

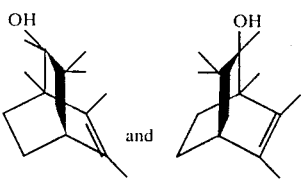

The reaction of the compound having the structure:

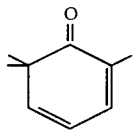

with the compound having the structure:

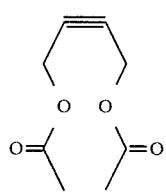

may be carried out in the presence or in the absence of a reaction vehicle. Such a vehicle can function as a solvent for the reactions, to moderate the course of the reaction, to provide more intimate contact between the reactants and to improve control over parameters such as temperature and pressure. The reaction vehicle should be inert and is desirably one in which both reactants are soluble. The reaction vehicle in this reaction may be an aromatic hydrocarbon such as benzene or a substituted aromatic hydrocarbon particularly an alkyl substituted benzene such as toluene, xylene or the like.

The pressure under which the Diels-Alder reaction between the compound having the structure:

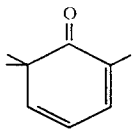

and the compound having the structure:

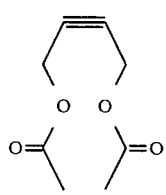

is carried out can vary over a range and is desirably superatmospheric. Pressures of from 150 to 400 psig are desirably used.

The Diels-Alder reaction can be carried out at temperatures of from about 150° C. up to about 300° C. Below the aforesaid lower temperature, the reaction proceeds at a very low rate.

On the other hand, at temperatures considerably higher than those preferred, the reaction may proceed uncontrollably and/or produce a relatively large quantity of unwanted by-products which lower the yield of desirable materials and complicate purification of the product. The preferred temperature of the instant reaction between the compound having the structure:

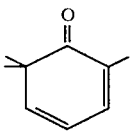

and the compound having the structure:

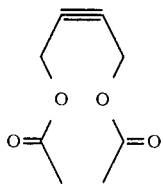

is between 190° C. and 210° C. The resultant reaction product having the structure:

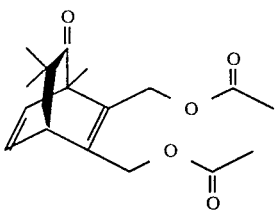

can be purified and/or isolated by conventional methods as hereinafter mentioned.

The stepwise hydrogenation of the compound having the structure:

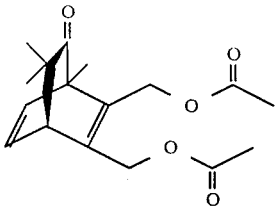

to form the intermediate having the structure:

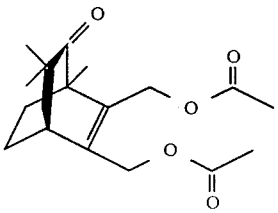

is carried out with gaseous hydrogen. The hydrogenation is desirably carried out at superatmospheric pressures of 150–600 psig and preferably from 200 to 400 psig to provide a good reaction rate without substantial production of unwanted by-products.

The temperature is chosen so as to provide reaction times of about 1 to 8 hours and preferably 2 to 6 hours. Accordingly, the temperatures utilized are in the range of 20°–40° C., preferably from 25°–30° C.

The hydrogenation is desirably carried out in the presence of an inert vehicle, desirably a lower aliphatic alcohol. Preferred vehicles are ethanol, propanol and isopropanol. The reaction is carried out in the presence of a catalyst and the metallic hydrogenation catalyst such as nickel or precious metal such as platinum or palladium. The metallic catalyst can be utilized on a carrier and a 5% palladium on carbon catalyst is utilized in certain preferred embodiments of our invention.

The intermediate having the structure:

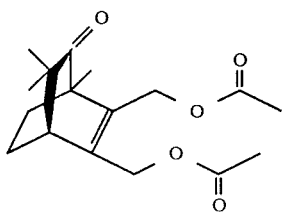

can be purified or isolated by conventional purification after appropriate washing, neutralizing or drying.

The intermediate having the structure:

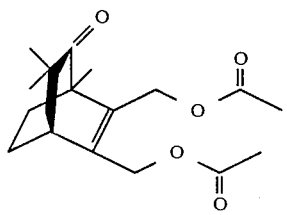

is further hydrogenated to form the ketone having the structure:

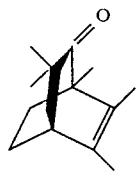

by means of additional hydrogenation at higher temperatures. The hydrogenation is carried out with gaseous hydrogen and is desirably carried out at superatmospheric pressures of from 150–600 psig and preferably from 200–400 psig to provide a good reaction rate without substantial production of unwanted by-products.

The temperature is chosen so as to provide reaction times of about 1 to 8 hours and preferably 2 to 6 hours. Accordingly, the temperatures utilized are in the range of 75° C. to 210° C. and preferably 75° C. to 120° C.

The hydrogenation is desirably carried out in the presence of an inert vehicle, desirably a lower aliphatic alcohol. Preferred vehicles are ethanol, propanol and isopropanol. The reaction is carried out in the presence of a catalyst and the metallic hydrogenation catalyst such as nickel or precious metals such as platinum or palladium are desirable. The metallic catalyst can be utilized on a carrier and a 5% palladium on carbon catalyst is utilized in certain preferred embodiments of our invention.

To obtain the 1,2,3,3,5,6-hexamethyl-bicyclo[2.2.2]oct-5-en-2ol according to our invention, the ketone defined according to the structure:

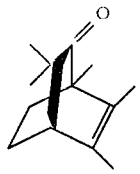

is reacted with an organometallic compound having the structure:

CH₃M wherein m may be MgX or Li and X is chloro, bromo or iodo. Examples of compounds wherein M is MgX are methyl magnesium chloride, methyl magnesium bromide and methyl magnesium iodide. Examples where M is Li is methyl lithium.

The reaction is preferably carried out in a vehicle. The vehicles are polar organic solvents and solvents having a boiling point at atmospheric pressure in the range of 130°–140° C. are preferred. The preferred solvent is xylene. Surprisingly, using a xylene solvent at a temperature in the range of 135°–140° C. at atmospheric pressure, an optimal ratio of isomers is obtained yielding optimal organoleptic (aroma) properties particularly concerning the aesthetic value of the long lasting intense, patchouli aroma quality of the isomer mixture. The reaction vehicle can also comprise phosphorous-containing materials such as hexamethyl phosphoramide and the like.

The reaction vehicle as noted above can also include aromatic solvents, particularly monocyclic materials such as benzene, toluene and the like.

The reaction with the organometallic compound is desirably carried out at temperatures of from 10° C. to about 200° C. The use of temperatures substantially below this desirable range results in extremely low reaction rates and the use of temperatures substantially above this range can result in undesirable by-products and unnecessarily high pressures. It is, accordingly, preferred to use temperatures in the range of from 80° C. to 150° C. and preferably from 130°–140° C.

The reaction can be carried out under a wide range of pressures depending on temperature and vehicles used but the atmospheric and superatmospheric pressures are preferred.

The quantity of compound having the structure:

CH₃M reacted with compound having the structure:

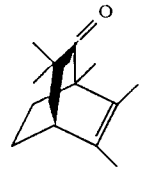

can be varied over a wide range. It is desirable to use at least a stoichiometric quantity of organometallic compound, and quantities up to 250% of such theoretical amount can be utilized, that is, a 150% excess. In general, it is desirable to use from about 125% to about 200% of the theoretical amount of organometallic compound to insure good reaction rates and completeness.

The time required for the reaction will vary depending upon the temperature, pressure and the like. Ordinarily, reaction times of from about 2 to about 24 hours are desirable. It will be understood from the present disclosure, that temperatures of 100° C. will permit obtaining good yields of organo-metalloid corresponding to the alcohol in four hours with relatively small excesses of organometallic compounds whereas longer times of 16 to 20 hours can be required with temperatures of 60° C. These organo-metalloids are defined according to the structures:

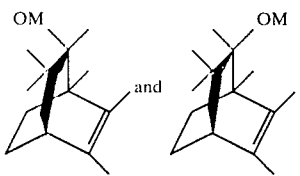

wherein M is defined as above.

After the reaction with the organometallic compound is completed to the extent desired, the product is then hydrolyzed by acidification or basification to obtain the alcohols themselves having the structures:

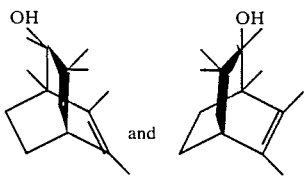

A base or an acid can be added to water and this can be used to wash and hydrolyze the salt, the product of the reaction. Such hydrolysis can be carried out over a wide range of temperatures from 5° C. to about 100° C. and temperatures of 15° C. to about 30° C. are preferred. In certain embodiments of the invention, the hydrolysis is carried out with an acidic medium such as saturated ammonium chloride solution.

As taught hereinafter, the isomers and mixtures of isomers of the present invention, the 1,2,3,3,5,6-hexamethyl-bicyclo[2.2.2]oct-5-en-2-ol of the present invention, has certain strong, patchouli, ginger and camphoreous aroma nuances which suit them for altering the aroma of consumable materials such as perfume compositions, colognes and perfumed articles, e.g. solid or liquid anionic, cationic, nonionic or zwitterionic detergents or fabric softener compositions or fabric softener articles, e.g. BOUNCE ® manufactured by the Procter & Gamble Company of Cincinnati, Ohio.

According to our invention, a "perfume composition" is composed of a small but effective amount of 1,2,3,3,5,6-hexamethyl-bicyclo[2.2.2]oct-5-en-2-ol produced according to this invention and an auxilliary perfume ingredient including, for example, alcohols other than the 1,2,3,3,5,6-hexamethyl-bicyclo[2.2.2]oct-5-en-2-ol isomers of our invention, aldehydes, ketones, nitriles, esters and frequently hydrocarbons which are admixed so that the combined odors of the individual components produce a pleasant or desired fragrance. Such perfume compositions usually contain (a) the main note or bouquet or foundation stone of the composition; (b) modifiers which round off and accompany the main notes; (c) fixatives which include odorous substances which lend a particular note to the perfume throughout all stages of evaporation and substances which retard evaporation and (d) topnotes which are usually low-boiling, fresh-smelling materials.

In perfume compositions, the individual component will contribute its particular olfactory characteristics but the overall effect of the perfume composition will be the sum of the effect of each ingredient. Thus, the 1,2,3,3,5,6-hexamethyl-bicyclo[2.2.2]oct-5-en-2-ol of this invention taken as individual isomers having the structures:

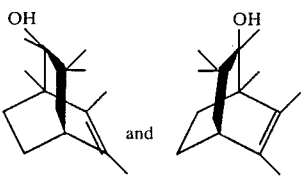

or mixtures of these isomers in various proportions can be used to alter the aroma characteristics of a perfume composition, for example, by highlighting or moderating the olfactory reaction contributed by another ingredient in the composition.

The amount of the 1,2,3,3,5,6-hexamethyl-bicyclo[2.2.2]oct-5-en-2-ol of our invention either in admixture or as individual isomers which will be effective in perfume compositions depends on many factors including the other ingredients, their amounts and the effects which are desired. It has been found that perfume compositions containing as little as 0.02% of the 1,2,3,3,5,6-hexamethyl-bicyclo[2.2.2]oct-5-en-2-ol of our invention, or even less, can be used to impart a scent odor to soaps, cosmetics, solid or liquid anionic, cationic, nonionic or zwitterionic detergents, perfumed polymers, fabric softener compositions and drier-added fabric softener articles such as BOUNCE ® and other products. The amount employed can range up to 5% or higher of the fragrance components and will depend on considerations of cost, nature of the end product, the effect desired on the finished product and the particular fragrance sought.

The 1,2,3,3,5,6-hexamethyl-bicyclo[2.2.2]oct-5-en-2-ol of our invention either taken as isomeric mixtures or considered as individual isomers having the structures:

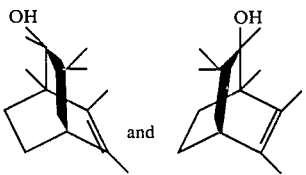

can be used alone or in a perfume composition as an olfactory composition for augmenting, enhancing or modifying the aromas of solid or liquid aionic, cationic, nonionic or zwitterionic detergents and soaps; space odorants and deodorants; perfumes; colognes; toilet waters; bath preparations such as bath oils and bath salts; hair preparations such as lacquers, brilliantines, pomades and shampoos; cosmetic preparations such as creams, deodorants, hand lotions and sun screens; powders such as talcs, dusting powders, face powders and the like. When used as an olfactory component of a perfumed article, as little as 50 ppm of the 1,2,3,3,5,6-hexamethyl-bicyclo[2.2.2]oct-5-en-2-ol of our invention will suffice to impart a strong, camphoraceous, patchouli and ginger aroma character. Generally, no more than 5% of the perfumed article is required. Thus the range of 1,2,3,3,5,6-hexamethyl-bicyclo[2.2.2]oct-5-en-2-ol in a perfumed article varies from 50 ppm up to 5% by weight.

All parts, percentages, proportions and ratios herein given are by weight unless otherwise indicated.

In addition, the perfume composition or fragrance composition can contain a vehicle or carrier for the 1,2,3,3,5,6-hexamethyl-bicyclo[2.2.2]oct-5-en-2-ol alone or taken together with other ingredients. The vehicle can be a liquid such as an alcohol, a glycol or the like. Examples of glycols are propylene glycol. Examples of alcohols are non-toxic alcohols such as ethyl alcohol. The carrier can be an absorbent solid such as a gum or components for encapsulating the composition such as by coacervation using gelatin or such as by forming a polymer wall around a liquid center as by using a urea formaldehyde prepolymer.

The following examples are given to illustrate embodiments of the invention as it is presently preferred to practice it. It will be understood that these examples are illustrative and the invention is not to be considered as restricted thereto except as indicated in the appended claims.

EXAMPLE I

PREPARATION OF 1,3,3,5,6-PENTAMETHYL-BICYCLO[2.2.2]OCTA-5,7-DIEN-2-ONE

Reaction:

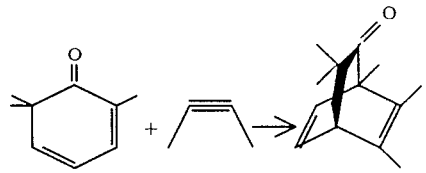

Into a 450 ml Parr mini-pressure reactor is placed 25 grams of 2,6,6-trimethylcyclohexa-2,4-dien-1-one dimer, 75 ml of toluene and 12.4 grams of 2-butyne.

The Parr reactor is sealed, flushed with nitrogen and heated to 180° C. After two hours at 180° C., GLC analysis indicates mostly starting material and the temperature is raised to 200° C. After twelve hours at 200° C., the reaction is approximately 70% complete. The reaction pressure at 200° C. is in the range of 120–150 psig.

The reaction mass is cooled and after cooling, an additional 2.4 grams of 2-butyne is added. The reaction mixture is then heated at 200° C. for an additional 14 hours at 120–150 psig. The reaction mass is then cooled to room temperature and the toluene is removed in vacuo to yield 29.9 grams of crude material.

A Rushover distillation gives 9.9 grams of 1,3,3,5,6-pentamethyl-bicyclo[2.2.2]octa-5,7-dien-2-one boiling at 55°–62° C. at 0.1 mm/Hg pressure. GLC analysis shows the material to be 93% pure. Pure samples obtained by preparative GLC have the following physical properties:

IR spectrum (thin film): 3050 cm$^{-1}$, 2975, 2935, 2862, 1725, 1440, 1378, 1009.

Mass spectrum: molecular ion at 190 m/e; then in descending order, 105, 120, 70, 42.

Actual distillation fractions are as follows:

| Vapor Temp. (°C.) | Liquid Temp. (°C.) | Pressure mm/Hg. |
|---|---|---|
| 47 | 77 | 0.1 |
| 55 | 105 | 0.1 |
| 62 | 120 | 0.1 |
| 56 | 133 | 0.1 |
| 45 | 149 | 0.1 |

FIG. 1 is the GLC profile for the reaction mass prior to distillation. Conditions: SE-30 column programmed from 120° C. to 210° C. at 8° C. per minute. The peak indicated by reference numeral "101" is the peak for the ketone defined according to the structure:

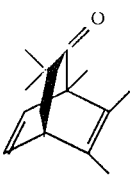

FIG. 2 is the mass spectrum for the compound having the structure:

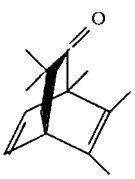

FIG. 3 is the infra-red spectrum for the compound having the structure:

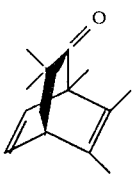

of peak 101 of FIG. 1.

FIG. 4 is the NMR spectrum for the compound of peak 101 of FIG. 1 having the structure:

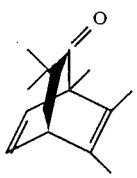

(Solvent CFCl$_3$; Field Strength 100 MHz).

EXAMPLE II

PREPARATION OF 1,3,3,5,6-PENTAMETHYL-BICYCLO[2.2.2]OCTA-5-EN-2-ONE

Reaction:

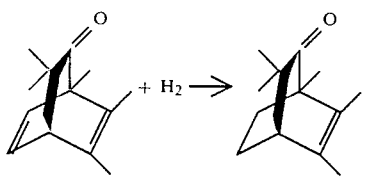

A solution of 37 grams of 1,3,3,5,6-pentamethyl-bicyclo[2.2.2]octa-5,7-dien-2-one prepared according to Example I in 120 ml of isopropyl alcohol and 0.5 grams of 10% palladium on carbon are placed in a hydrogenation apparatus and hydrogenated at 140–200 psig at a temperature in the range of 20°–35° C.

After a period of 69 minutes, the hydrogen uptake ceases and GLC analysis indicates that all of the starting material has been consumed. After filtering to remove the catalyst, the isopropyl alcohol is removed at 25 mm/Hg pressure and the residue is distilled at reduced pressure (boiling point 55°–58° C. at 0.1 mm/Hg) in order to yield 27.5 grams of product containing 92% 1,3,3,5,6-pentamethyl-bicyclo[2.2.2]octa-5-en-2-one as analyzed by means of GLC analysis.

Pure samples are obtained by preparative GLC.

The first distillation is carried out using a Vigreux equipped with fraction cutter yielding the following fractions:

| Fraction Number | Vapor Temp. (°C.) | Liquid Temp. (°C.) | Pressure mm/Hg | Weight of Fraction (grams) | % Product |
|---|---|---|---|---|---|
| 1 | 47/65 | 93/91 | 4/2 | 0.8 | 14 |
| 2 | 56–60 | 89 | 0.6 | 0.4 | 44 |
| 3 | 65–74 | 93 | 2/2 | 0.8 | 53 |
| 4 | 70/71 | 91/91 | 1/1 | 1.3 | 81 |
| 5 | 55/56 | 91/91 | 0.25/0.3 | 1.7 | 90 |
| 6 | 56 | 92 | 0.1/0.3 | 3.2 | 93 |
| 7 | 58 | 92 | 0.25/0.1 | 3.9 | 94 |
| 8 | 58 | 93 | 0.1 | 5.0 | 94 |
| 9 | 58 | 93 | 0.2 | 4.9 | 94 |
| 10 | 52 | 93 | 0.1 | 8.8 | 93 |
| 11 | 53 | 110 | 0.1 | 4.0 | 85 |
| 12 | 57 | 125 | 0.1 | 2.0 | 67 |

Fractions 5, 6, 7, 8, 9 and 10 are bulked to yield the 27.5 grams of 93% pure product.

FIG. 5 is the GLC profile for the reaction product of this example subsequent to solvent stripping but prior to distillation. The peak indicated by reference numeral "501" is the peak for the ketone having the structure:

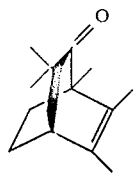

FIG. 6 is the mass spectrum for the compound of peak 501 of FIG. 5; having the structure:

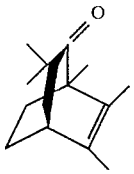

FIG. 7 is the NMR spectrum for the compound of peak 501 of FIG. 5 having the structure:

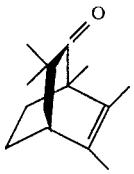

(Solvent CFCl$_3$; Field Strength 100 MHz).

FIG. 8 is the infra-red spectrum for the compound of peak 501 of FIG. 5 having the structure:

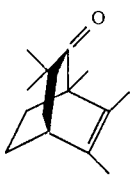

EXAMPLE III

PREPARATION OF 1,2,3,3,5,6-HEXAMETHYL-BICYCLO[2.2.2]OCT-5-EN-2-OL

Reactions:

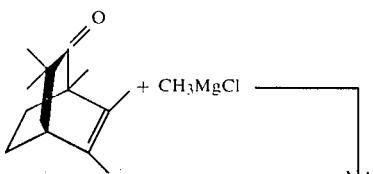

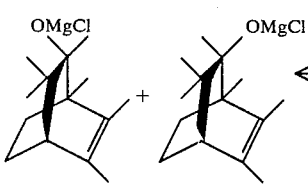

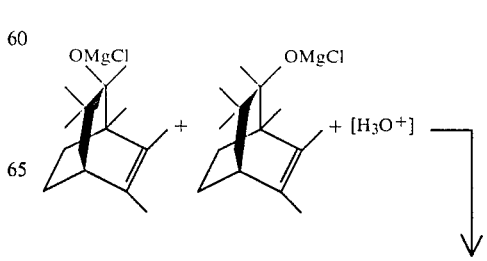

-continued

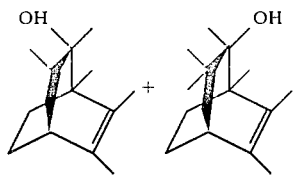

To a solution of 3.0 grams (15.6 milimoles) of 1,3,3,5,6-pentamethyl-bicyclo[2.2.2]oct-5-en-2-one prepared according to Example II in 5.5 ml of tetrahydrofuran under a nitrogen atmosphere is added 7.8 ml of 3.0 molar methyl magnesium chloride in tetrahydrofuran over a 2 minute period.

The resulting mixture is then heated to 70° C. for a period of 5 hours. After cooling the reaction mass to room temperature, the reaction mass is quenched with 60 ml of saturated ammonium chloride solution. The resulting top oil layer is separated and the bottom aqueous layer is extracted with 25 ml of methylene chloride. The extract and oil layers are combined, washed with 20 ml saturated sodium chloride solution, dried with anhydrous sodium sulfate and concentrated in vacuo to yield 3.0 grams of crude 1,2,3,3,5,6-hexamethyl-bicyclo[2.2.2]oct-5-en-2-ol, a mixture of isomers having the structures:

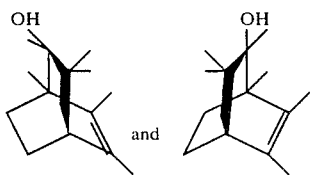

Distillation of this material in a short path distillation apparatus yields 1.8 grams of a material boiling at 113° C. at 5.7 mm/Hg. GLC analysis on a Carbowax 20M column, ¼" × 8' stainless steel column programmed from 120°–220° C. at 8° C. per minute shows that the material is a mixture of 2 compounds in a 1:7 ratio. The two components are isolated by preparative GLC on a Carbowax column and prove to be the isomeric forms of the product having the structures:

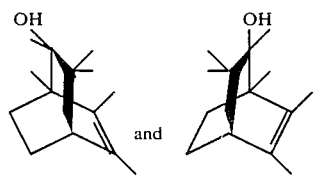

FIG. 9 is the GLC profile for fraction 2 of the aforedescribed distillation. The peaks indicated by reference numerals "901" and "902" are the peaks for the compounds having the structures:

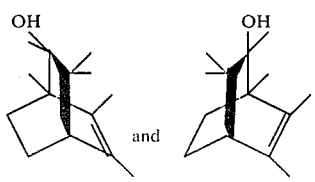

FIG. 10 is the mass spectrum for the compound of peak 901 of FIG. 9 having the structure:

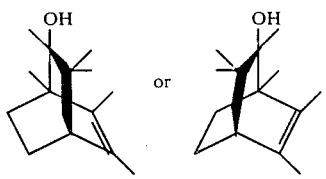

FIG. 11 is the infra-red spectrum for the compound of peak 901 of FIG. 9 having the structure:

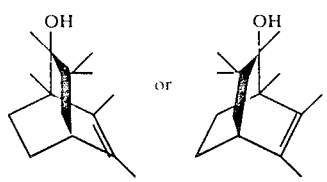

FIG. 12 is the NMR spectrum for the compound of peak 901 of FIG. 9 having the structure:

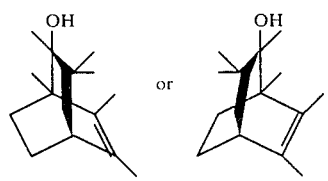

(Solvent $CFCl_3$; Field Strength 100 MHz).

FIG. 13 is the mass spectrum for the peak indicated by reference numeral 902 of FIG. 9 for the compound having the structure:

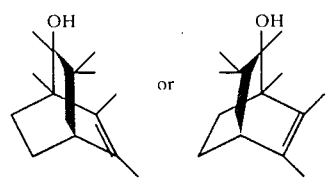

FIG. 14 is the infra-red spectrum for the compound of peak 902 of FIG. 9 having the structure:

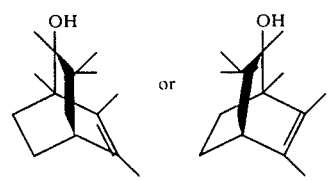

FIG. 15 is the NMR spectrum for the compound of peak 902 of FIG. 9 having the structure:

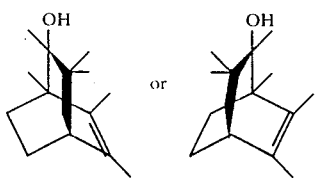

EXAMPLE IV

PREPARATION OF 5,6-BIS(HYDROXYMETHYL)-1,3,3-TRIMETHYL-BICYCLO[2.2.2]OCTA-5,7-DIEN-2-ONE DIACETATE

Reaction:

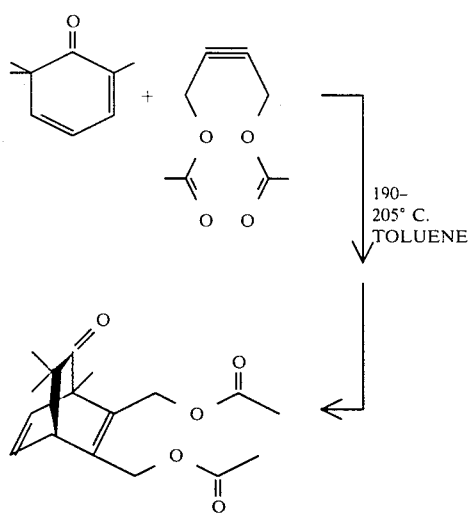

To a 450 ml Parr mini-pressure reactor is charged 30 grams of 2,6,6-trimethylcyclohexa-2,4-dien-1-one dimer, 105 ml of toluene and 46.8 grams of 2-butyne-1,4-dioldiacetate. The reactor is sealed, flushed with nitrogen and heated to 190° C. at 75-95 psig. After 3.7 hours, the reaction temperature is raised to 205° C. for 0.5 hours. The reaction mixture is then cooled to room temperature, transferred to a round bottom flask and the toluene is removed in vacuo to yield 77 grams of crude 5,6-bis(hydroxymethyl)-1,3,3-trimethylbicyclo-octa-5,7-dien-2-one diacetate.

A pure sample is isolated by preparative GLC (8'×¼" 25% SE-30 column, isothermal at 210° C.).

FIG. 16 is the GLC profile for the reaction product prior to distillation. The peak indicated by reference numeral "162" is the peak for the product of reaction defined according to the structure:

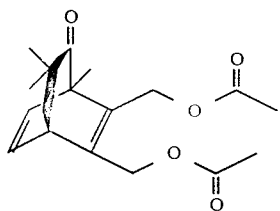

The peak indicated by reference numeral "161" is the peak for the starting material having the structure:

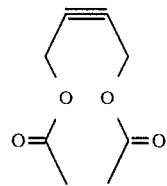

FIG. 17 is the mass spectrum for the peak indicated by reference numeral "162" of FIG. 16 defined according to the structure:

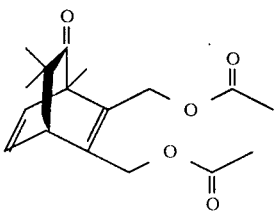

FIG. 18 is the infra-red spectrum for the compound of the peak indicated by reference numeral "162" of FIG. 16 having the structure:

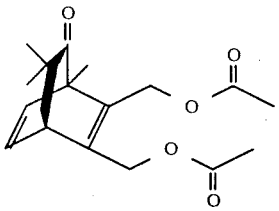

FIG. 19 is the NMR spectrum for the compound of the peak indicated by reference numeral "162" of FIG. 16 having the structure:

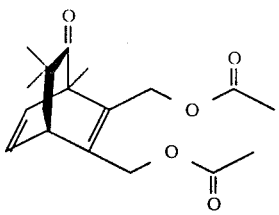

(Solvent: CFCl₃; Field Strength 100 MHz).

EXAMPLE V

PREPARATION OF 5,6-BIS(HYDROXYMETHYL)-1,3,3-TRIMETHYL-BICYCLO[2.2.2]OCTA-5-EN-2-ONE DIACETATE

Reaction:

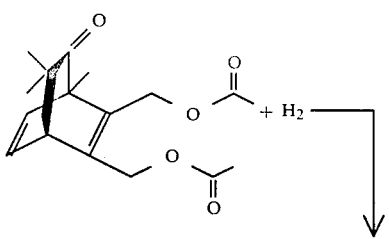

-continued

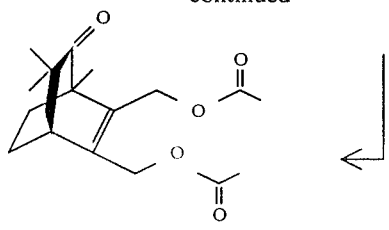

To a 450 ml Parr mini-pressure reactor is charged 15 grams of 5,6-bis(hydroxymethyl)-1,3,3-trimethylbicyclo[2.2.2]octa-5-dien-2-one diacetate produced according to Example IV, 60 ml of isopropyl alcohol and 0.3 grams of 10% palladium-on-carbon.

The reactor is flushed with nitrogen and then with hydrogen. Hydrogen is then charged to a pressure of 190 psig and stirring is initiated. A 50 psi pressure drop occurs within three minutes as the temperature rises from 22° to 27° C. There is no additional pressure drop during the next 3.3 hours, during which the reaction takes place at 140 psig and 22°-30° C.

The reaction mass is filtered and after filtering, the reaction mass is concentrated in vacuo to yield 13.6 grams of crude 5,6-bix(hydroxymethyl)-1,3,3,-trimethyl-bicyclo-[2.2.2]octa-5-en-2-one diacetate.

A pure sample is isolated by preparative GLC (8'×¼" 25% SE-30 column operated isothermally at 210° C.).

FIG. 20 is the GLC profile for the reaction product of this example. The peak indicated by reference numeral "201" is the peak for the compound having the structure:

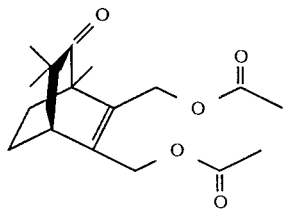

FIG. 21 is the infra-red spectrum for the compound of peak 201 of FIG. 20 having the structure:

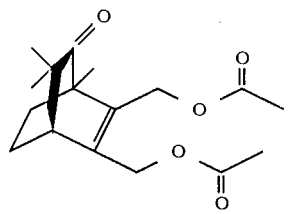

FIG. 22 is the NMR spectrum for the compound of peak 201 of FIG. 20 having the structure:

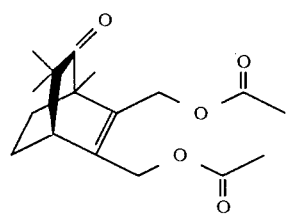

(Solvent: CFCl₃; Field Strength 100 MHz).

FIG. 23 is the mass spectrum for the compound of peak 201 of FIG. 20 having the structure:

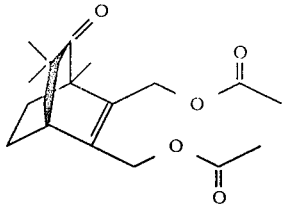

EXAMPLE VI

ONE STEP PREPARATION OF 1,3,3,5,6-PENTAMETHYL-BICYCLO[2.2.2]OCTA-5-EN-2-ONE

Reactions:

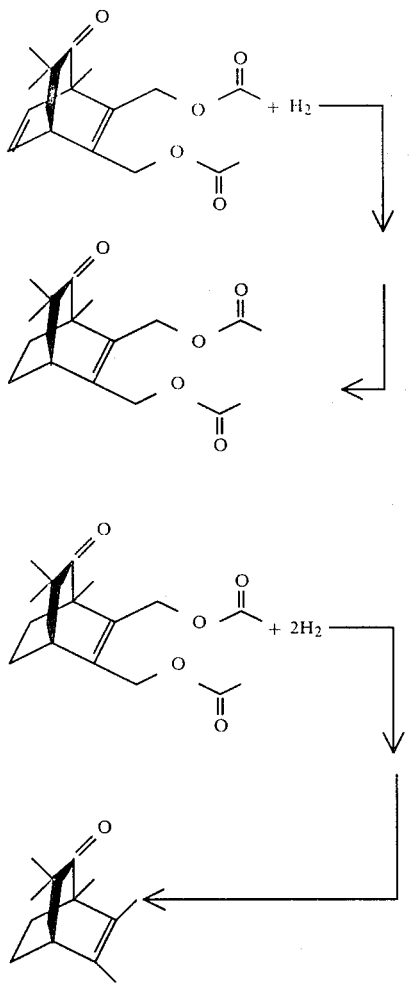

To a 450 ml Parr mini-pressure reactor is charged 15 grams of 5,6-bis(hydroxymethyl)-1,3,3-trimethylbicyclo[2.2.2]-octa-5,7-dien-2-one diacetate produced according to Example IV, 60 ml of isopropyl alcohol and 0.3 grams of 10% palladium on charcoal. After flushing with nitrogen and hydrogen, the hydrogen is charged to a pressure of 195 psig while maintaining the reaction mass temperature at 22°-27° C. Within four minutes, the pressure drops to 140 psig and holds steady for six minutes. Hydrogen is again charged to 195 psig and the temperature is gradually raised to 80° C. At 80° C. the pressure begins to drop. The temperature is raised to 85° C. and maintained at 85° C. until the pressure holds constant at 102 psig (1.7 hours). After cooling to room temperature, the reaction mass is filtered and the toluene is removed in vacuo to yield 10.1 grams of 1,3,3,5,6-pentamethyl-bicyclo[2.2.2]octa-5-en-2-one. This material is identical to that prepared from 2,6,6-trimethylcyclohexa-2,4-dien-1-one and 2-butyne according to Examples I and II, supra.

FIG. 24 is the GLC profile for the reaction product of this example. The peak indicated by reference numeral "241" is the peak for the compound having the structure:

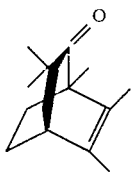

EXAMPLE VII

PERFUME COMPOSITION

A perfume composition is prepared by admixing the following ingredients in the indicated proportions:

| Ingredient | Amount (Grams) |
|---|---|
| n-decyl aldehyde | 1.0 |
| n-dodecyl aldehyde | 2.0 |
| methyl nonyl acetaldehyde | 0.5 |
| linalool | 50.0 |
| linalyl acetate | 70.0 |
| phenyl ethyl alcohol | 100.0 |
| Pettigrain SA | 20.0 |
| Bergamot oil | 30.0 |
| alpha methyl ionone | 25.0 |
| mixture of isomers of 1',2',3',4' 5',6',7',8'-octahydro-2',3',8',8'-tetramethyl-2'-acetonaphthones produced by the process of Example II (prior to GLC separation) of U.S. Pat. No. 3,911,018 issued on October 7, 1975 | 10.0 |
| cyclized bicylclo C-12 material produced according to the process of Example IV of Canadian Patent 854,225 issued October 20, 1970 | 5.0 |
| iso bornyl cyclohexyl alcohol | 10.0 |
| benzyl acetate | 25.0 |
| 2-n-heptyl cyclopentanone | 5.0 |
| hexahydro-2,5,5-trimethyl-2H—2,4-a-methanonaphthalene-1(5H)-one prepared according to Example VIII of U.S. Pat. No. 4,285,349 | 12.5 |
| mixture of tricyclic alcohol isomers prepared according to Example III having the structures: [OH structure and OH structure] | 12.5 |

The foregoing blend is evaluated and found to have a high degree of richness and persistence in its novel patchouli, amber, camphoraceous and ginger-like character. It also has excellent unique leathery notes in addition to the patchouli, camphoraceous and ginger-like notes contributed by the mixture of isomers prepared according to Example III.

This base composition can be admixed with aqueous ethanol, chilled and filtered to produce a finished cologne. The cologne so prepared has an amber aroma with strong patchouli-like, ginger-like, camphoraceous and leathery nuances. The base composition can also be used to scent soap or other toilet goods such as lotions, aerosols, sprays and the like.

EXAMPLE VIII

PREPARATION OF A COSMETIC POWDER

A cosmetic powder is prepared by mixing in a ball mill, 100 grams of talcum powder with 0.25 grams of one of the products listed below in Table I. The resulting material has an excellent perfume aroma as set forth in Table I below.

TABLE I

| Description of Composition | Fragrance Characteristics |
|---|---|
| Mixture of tricyclic alcohols produced according to Example III defined according to the structures: [OH structure and OH structure] | A strong patchouli-like, camphoraceous, ginger-like aroma. |
| Perfume composition of Example VI | A strong, ambery, leather aroma with patchouli, |

TABLE I-continued

| Description of Composition | Fragrance Characteristics |
|---|---|
| | ginger-like and camphoraceous nuances. |

EXAMPLE IX
PERFUMED LIQUID DETERGENT

Concentrated liquid detergents with aromas as set forth in Table I of Example VIII (which detergents are produced from the lysine salt of n-dodecyl benzene sulfonic acid as more specifically described in U.S. Pat. No. 3,948,818 issued on Apr. 6, 1976, the disclosure of which is incorporated by reference herein) are prepared containing the substances set forth in Table I of Example VIII supra. They are prepared by adding and homogeneously mixing the appropriate quantity of substance of Table I of Example VIII in the liquid detergent. The detergents all possess excellent aromas as set forth in Table I of Example VIII.

EXAMPLE X
PREPARATION OF COLOGNE AND HANDKERCHIEF PERFUME

Perfume substances as set forth in Table I of Example VIII are incorporated into colognes at concentrations of 1.5%, 2.0%, 2.5%, 3.0%, 3.5%, 4.0% and 5.0% in 80%, 85%, 90% and 95% aqueous food grade ethanol; and into handkerchief perfumes at concentrations of 10%, 15%, 20%, 30%, 40% and 50% (in 90% and 95% aqueous food grade ethanol). Distinct and definitive fragrance aromas as set forth in Table I of Example VIII are imparted to the cologne and to the handkerchief perfumes.

EXAMPLE XI
PREPARATION OF SOAP COMPOSITION

One hundred grams of soap chips (obtained from IVORY ® soap) (a trademark of the Procter & Gamble Company of Cincinnati, Ohio) are mixed with two grams of the materials as set forth in Table I of Example VIII until a substantially homogeneous composition is obtained. The resulting composition is melted at 180° C. for a period of four hours under 15 atmospheres nitrogen pressure. The resulting melt is cooled and formed into soap bars. Each of the soap bars has an aroma as set forth in Table I of Example VIII.

EXAMPLE XII
PREPARATION OF LIQUID DETERGENTS

Concentrated liquid detergents with aromas as set forth in Table I of Example VIII containing 0.2%, 0.5% and 1.2% of the substances set forth in Table I of Example VIII are prepared by adding the appropriate quantity of the indicated composition as set forth in Table I of Example VIII to a liquid detergent known as P-87. The aromas of the liquid detergent increase with increasing concentration of the composition as set forth in Table I of Example VIII.

EXAMPLE XIII
FABRIC SOFTENER ARTICLE

Utilizing the procedure of Example I at column 15 of U.S. Pat. No. 3,632,396 (the disclosure of which is incorporated by reference herein), a non-woven cloth substrate useful as a drier-added fabric softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57% $C_{20-22}$HAPS
   22% isopropyl alcohol
   20% antistatic agent
   1% of composition as set forth in Table I of Example VIII.

Fabric softening compositions prepared as set forth below having the aroma characteristics as set forth in Table I of Example VIII essentially consist of a substrate having a weight of about 3 grams per 100 square inches; a substrate coating of about 1.85 grams per 100 square inches of substrate; and an outer coating of about 1.4 grams per 100 square inches of substrate thereby providing a total aromatized substrate and outer coating weight ratio of about 1:1 by weight of the substrate. The aromas as set forth in Table I of Example VIII are imparted in a pleasant manner to the head space in the drier on operation thereof using the said drier added fabric softening non-woven fabric.

EXAMPLE XIV
SOLID DETERGENT

Granular detergent compositions prepared according to United Kingdom Patent Specification No. 1,501,498 having the following formulae are prepared by spray-drying the following mixture:

| Ingredient | Percent by Weight |
|---|---|
| Sodium salt of ethoxylated fatty alcohol sulfate having an average of about 2.25 moles of ethylene oxide per mole of fatty alcohol (1) | 14.1 |
| Sodium tallow alkyl sulfate | 2.4 |
| Sodium silicate solids ratio: $SiO_2/Na_2O = 2.0$ | 0.0 |
| Sodium silicate solids ratio: $SiO_2/Na_2O = 3.2$ | 1.0 |
| Sodium tripolyphosphate | 24.0 |
| $Na_{12}(AlO_2.SiO_2)_{12}.27H_2O$ (2) | 18.0 |
| Moisture | 10.0 |
| Sodium sulfate | 25.0 |
| Minor ingredients including sodium toluene sulfonate, trisodium sulfosuccinate, dyes, brighteners | 4.0 |
| Perfume substance as set forth in Table I of Example VIII | 1.5 |

(1) Fatty alcohol composition: 66% $C_{14}$; 33% $C_{16}$; 1% $C_{18}$.
(2) Prepared as described in United Kingdom Patent 1,501,498; average particle size diameter 2 microns.

Laundry solutions containing the above detergent composition are used to launder fabrics. Each of the laundry compositions both prior to and on laundering give rise to the aromas as set forth in Table 1 of Example VIII.

EXAMPLE XV
PERFUMED LIQUID DETERGENT

Concentrated liquid detergents having aromas as set forth in Table 1 of Example VIII are prepared containing 0.10%, 0.15%, 0.20%, 0.40% and 0.80% of one of the materials set forth in Table I of Example VIII. They are prepared by adding and homogeneously mixing the appropriate quantity of perfume substance in liquid detergent. The liquid detergent is a builder-free liquid detergent consisting of (a) 50% of a nonionic surfactant having an HLB of 8.0 and a critical micelle concentration of 0.007, weight percent at 25° C.; (b) an ionic surfactant which is triethanolamine citrate; and (c) one weight percent of diethanolamine prepared according to United Kingdom Patent Specification No. 1,491,603 (the specification for which is incorporated herein by reference).

The detergents all possess fragrances as set forth in Table I of Example VIII, the intensity increasing with greater concentrations of fragrance material.

EXAMPLE XVI

PREPARATION OF 1,2,3,3,5,6-HEXAMETHYL BICYCLO[2.2.2]OCT-5-EN-2-OL

Reactions:

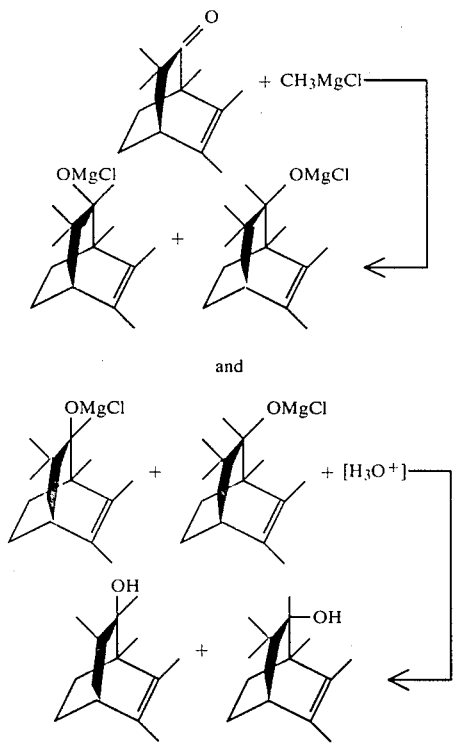

Into a 5 liter, three-neck round bottom flask equipped with mechanical stirrer, "Y" tube, thermometer, one-liter addition funnel equipped with nitrogen inlet, Claissen head, Friedrich's condenser, heating mantle and 6" 24/40 Vigreux column is placed 2,115 ml of commercial xylenes (mixture of ortho, meta and para xylene) (distilled) and 383 grams (1.995 moles) of the ketone having the structure:

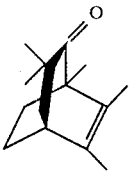

prepared according to Example VI.

The reaction mixture is heated to the range of 118°–133° C. and over a five hour period, 800 ml of a three molar solution of methyl magnesium chloride and tetrahydrofuran (2.4 moles of methyl magnesium chloride) is added to the reaction mass while simultaneously distilling and replacing the xylene from the reaction mixture and into the reaction mixture (in order to remove low-boiling tetrahydrofuran and keep the temperature of the reaction at about 130°–135° C.). At the end of the five hour period, 4,300 ml of xylene was distilled out, replaced by 3,700 ml xylene.

The reaction mass is then cooled on a water/ice bath and 1,000 ml saturated aqueous ammonium chloride is added to the reaction mass over a period of one hour while maintaining the reaction mass temperature at 25°–49° C.

2,250 ml of the reaction mass is transferred to a 5 liter separatory funnel and 1,000 ml water is added thereto. There now exists two sections of the reaction product; one in the five liter reaction flask and the second in the five liter separatory funnel.

1,700 ml water is added to the substance in the five liter flask followed by:
45 ml 6 normal HCl
500 ml water
30 ml concentrated HCl
20 ml concentrated HCl
50 ml saturated ammonium chloride.

To the substance in the five liter separatory funnel, 1,800 ml water is added followed by:
25 ml 6 normal HCl
150 ml water
10 ml concentrated HCl
50 ml saturated aqueous ammonium chloride.

The organic layers are combined and placed in a five liter separatory funnel. 500 ml water is added and the organic layer is separated from the aqueous layer. All of the aqueous phases formed above are combined and extracted with two 500 ml portions of xylene. The xylene extracts are combined with the organic layer and the combined organic layers are washed twice with 1,000 ml water. The organic phase is then filtered through coarse filter paper and dried on anhydrous sodium sulfate and then stripped of xylene. GLC of the crude alcohol indicates an isomer ratio of 1:4.

The organic phase is then distilled yielding the following fractions:

| Fraction Number | Vapor Temp. (°C.) | Liquid Temp. (°C.) | Pressure mm/Hg | % Isomer 1 | % Isomer 2 | Total % Tricyclic Alcohol | Wt. of Fract. (grams) |
|---|---|---|---|---|---|---|---|
| 1 | 100/110 | 115/116 | 8/8 | 16.5 | 63.5 | 80.0 | 10.4 |
| 2 | 111.0 | 117.0 | 8 | 17.7 | 76.8 | 94.5 | 14.8 |
| 3 | 111.0 | 117.0 | 8 | 17.9 | 78.8 | 96.7 | 21.0 |
| 4 | 111.5 | 117.5 | 8 | 20.2 | 77.9 | 97.9 | 36.6 |
| 5 | 112.0 | 118.5 | 8 | 16.7 | 81.6 | 98.3 | 54.2 |

-continued

| Fraction Number | Vapor Temp. (°C.) | Liquid Temp. (°C.) | Pressure mm/Hg | % Isomer 1 | % Isomer 2 | Total % Tricyclic Alcohol | Wt. of Fract. (grams) |
| --- | --- | --- | --- | --- | --- | --- | --- |
| 6 | 113.0 | 121.0 | 8 | 19.5 | 77.6 | 97.1 | 83.0 |
| 7 | 113.5 | 126.5 | 8 | 19.2 | 77.0 | 96.2 | 68.6 |
| 8 | 115.5 | 143.5 | 8 | 18.3 | 75.6 | 93.9 | 40.6 |
| 9 | 117.0 | 152.0 | 8 | 18.0 | 72.6 | 90.6 | 6.4 |
| 10 | 110.0 | 164.0 | 1 | 17.2 | 65.9 | 83.1 | 13.9 |

Fractions 6 and 7 are bulked for subsequent organoleptic utilization.

Bulked fractions 6 and 7 have a strong camphoraceous, patchouli, ginger aroma with intense, long-lasting, camphoraceous and patchouli nuances on dry-out.

GLC, NMR, IR and mass spectral analyses yield the information that the product is identical to the product produced according to Example III in that it contains the isomers having the structures:

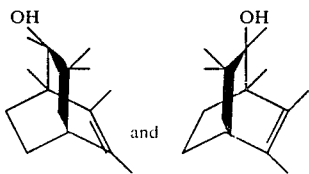

EXAMPLE XVII

HONEY PERFUME BASE FORMULATION

The following honey perfume base formulation is prepared:

| Ingredients | Parts by Weight |
| --- | --- |
| 1,2,3,3,5,6-hexamethyl-bicyclo[2.2.2]oct-5-ene-2-ol, bulked fractions 6 and 7 prepared according to Example XVI | 100 |
| Coumarin | 100 |
| Benzyl benzoate | 400 |
| Phenylethylphenyl acetate | 100 |
| Phenylethyl alcohol | 100 |
| Dimethylbenzylcarbinyl acetate | 180 |
| Phenylacetaldehyde dimethyl acetal | 55 |
| Phenylacetaldehyde diisopropyl acetal | 32 |
| Methyl anthranilate | 82 |
| 1,3,3,5-tetramethyl-7-cyano-bicyclo-[2.2.2]-octane | 41 |

The 1,2,3,3,5,6-hexamethyl-bicyclo[2.2.2]oct-5-ene-2-ol prepared according to Example XVI, bulked fractions 6 and 7 add an intense, strong, camphoraceous, ginger-like, patchouli-like character so necessary for this natural honey formulation to cause it to have a natural honey/patchouli character.

EXAMPLE XVIII

Scented polyethylene pellets having a pronounced patchouli aroma with camphoraceous and ginger nuances are prepared as follows:

In accordance with Example III of U.S. Pat. No. 3,505,432, the specification for which is incorporated by reference herein, 75 pounds of polyethylene having a melting point of about 220° F. are heated to about 230° F. in a container of the kind illustrated in FIGS. 1 and 2 of U.S. Pat. No. 3,505,432. 25 pounds of the 1,2,3,3,5,6-hexamethyl-bicyclo[2.2.2]oct-5-en-2-ol prepared according to Example XVI, bulked fractions 6 and 7 are then quickly added to the liquefied polyethylene, the lid is put in place and the agitating means are actuated. The temperature is maintained at about 225 F. and the mixing is continued for about 5–15 minutes. The valve at the bottom of the container is then opened to allow flow of the molten polyethylene enriched with the tricyclic alcohol-containing material to exit through the orifices at the bottom of the holding tank. The liquid falling through the orifices solidifies almost instantaneously upon impact with the moving, cooled conveyor. Solid polyethylene beads or pellets having a pronounced patchouli aroma with ginger and camphoraceous undertones are thus formed. Analysis demonstrates that the pellets contain about 25% of the 1,2,3,3,5,6-hexamethyl-bicyclo[2.2.2]oct-5-en-2-ol so that almost no losses of the scenting substance occur. These pellets may be called master pellets. 50 pounds of the patchouli scent-containing master pellets are then added to 1,000 pounds of unscented polyethylene powder and the mass is heated to the liquid state. The liquid is molded into thin sheets of films. The thin sheets of films have a pronounced patchouli aroma with ginger/camphoraceous undertones.

EXAMPLE XIX 100 pounds of polypropylene are heated to about 300° F. 30 pounds of the perfume composition described in Example XVII are added to the liquified polypropylene. This procedure is carried out in the apparatus shown in FIGS. 1 and 2 of U.S. Pat. No. 3,505,432. After mixing for about 8 minutes, the valve at the bottom of the container is opened to allow the exit of the polypropylene-scented material mixture whereby solid pellets having a pronounced honey/patchouli aroma are formed on the conveyor belt. The pellets thus obtained are then admixed with about 20 times their weight of unscented polypropylene and the mixture is heated and molded into flat discs. The flat discs have a strong and pleasant honey/patchouli aroma.

EXAMPLES XX, XX(A) AND XX(B)

PREPARATION OF 1,2,3,3,5,6-HEXAMETHYL-BICYCLO[2.2.2]OCT-5-EN-2-OL

Reactions (for Examples XX, XX(A) and XX(B):

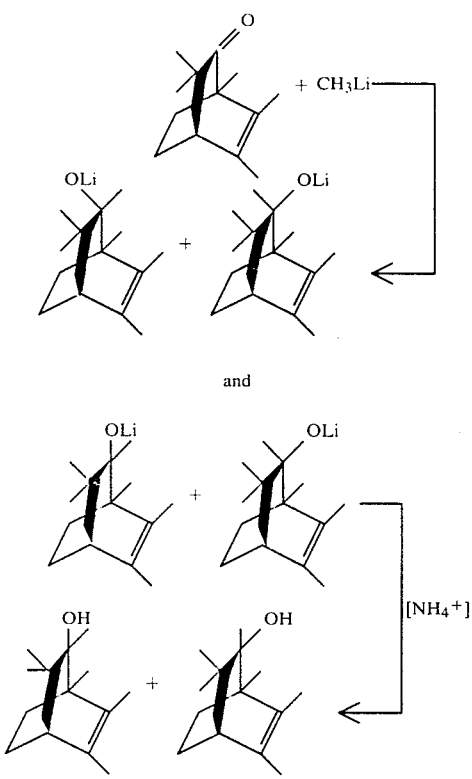

To a solution of 1.8 grams of 1,3,3,5,6-pentamethyl-bicyclo[2.2.2]-5-oct-5-en-2-one having the structure:

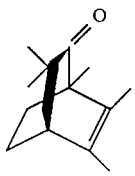

prepared according to Example VI, in 11 ml of tetrahydrofuran, maintained at −20° C. is added 9 ml of a 1.3 molar solution of methyl lithium in diethylether.

After stirring the reaction mass at −20° C. for a 10 minute period, a sample is taken and treated with saturated ammonium chloride. The organic oil is separated. GLC analysis of the oil (conditions: SE-30 column operated isothermally at 210° C.) shows a 1:3 ratio of isomers.

FIG. 25 is the GLC profile for this reaction product. The peak indicated by reference numeral "251" is the peak for the starting material having the structure:

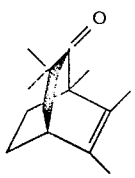

The peak indicated by reference numeral "252" is the peak for one of the isomers having the structure:

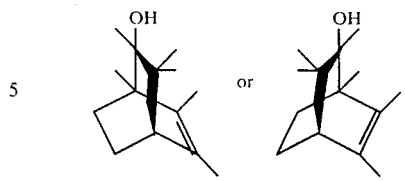

The peak indicated by reference numeral "253" is for one of the isomers having the structure:

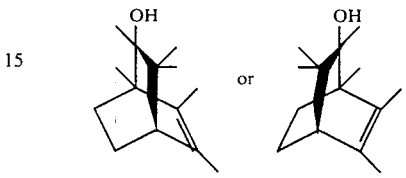

EXAMPLE XX(A)

The foregoing reaction is repeated at +30° C. instead of −20° C. GLC analysis of the oil (conditions: SE-30 column operated isothermally at 210° C.) shows a 1:2.2 ratio of isomers.

FIG. 26 is the GLC profile for this reaction mixture. The peak indicated by reference numeral "261" is the peak for the starting material having the structure:

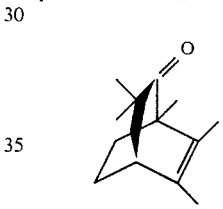

The peak indicated by reference numeral "262" is the peak for one of the isomers having the structure:

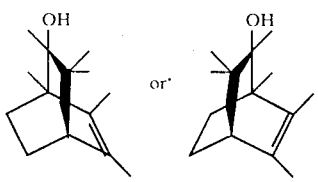

The peak indicated by reference numeral "263" is for one of the starting materials having the structure:

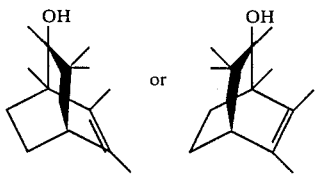

EXAMPLE XX(B)

The procedure of Example XX is carried out at +55° C. instead of −20° C. GLC analysis of the oil (conditions: SE-30 column operated isothermally at 210° C.) shows a 1:2.1 ratio of isomers. The peak indicated by reference numeral "272" is the peak for one of the isomers having the structure:

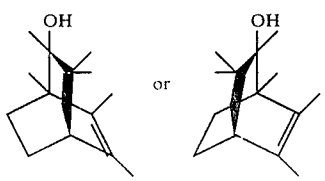

The peak indicated by reference numeral "273" is for one of the isomers having the structure:

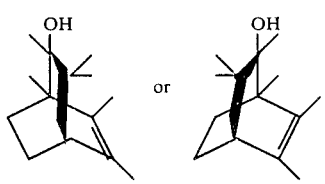

What is claimed is:
1. A compound defined according to a structure selected from the group consisting of:

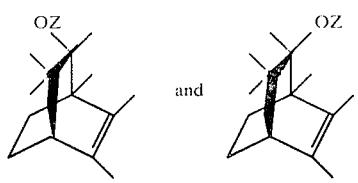

wherein Z represents hydrogen, MgX or Li and X represents chloro, bromo or iodo.

2. A compound defined according to claim 1 having a structure selected from the group consisting of:

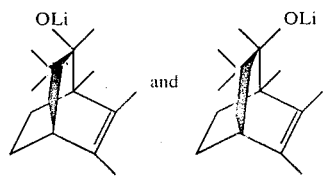

3. The compound of claim 1 having a structure selected from the group consisting of:

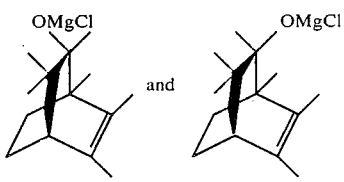

4. The compound of claim 1 having a structure selected from the group consisting of:

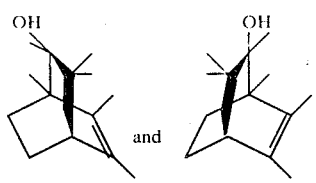

* * * * *